US008771703B2

(12) United States Patent
Couture et al.

(10) Patent No.: US 8,771,703 B2
(45) Date of Patent: Jul. 8, 2014

(54) SOLUBLE RECOMBINANT INFLUENZA ANTIGENS

(75) Inventors: Manon Couture, Québec (CA);
Nathalie Landry, Québec (CA);
Louis-Philippe Vezina, Québec (CA);
Michéle Dargis, Québec (CA)

(73) Assignee: Medicago Inc., Quebec (CA)

( * ) Notice: Subject to any disclaimer, the term of this patent is extended or adjusted under 35 U.S.C. 154(b) by 180 days.

(21) Appl. No.: 13/001,111

(22) PCT Filed: Jul. 7, 2009

(86) PCT No.: PCT/CA2009/000941
§ 371 (c)(1),
(2), (4) Date: Dec. 23, 2010

(87) PCT Pub. No.: WO2010/003235
PCT Pub. Date: Jan. 14, 2010

(65) Prior Publication Data
US 2011/0104753 A1 May 5, 2011

Related U.S. Application Data

(60) Provisional application No. 61/078,963, filed on Jul. 8, 2008.

(51) Int. Cl.
*A61K 39/145* (2006.01)
*A61K 39/00* (2006.01)
*C12N 15/82* (2006.01)
*C12N 15/79* (2006.01)
*C12N 15/84* (2006.01)
*C12N 15/44* (2006.01)
*C12N 15/62* (2006.01)
*C12N 15/90* (2006.01)
*C12N 5/10* (2006.01)
*C07K 14/005* (2006.01)

(52) U.S. Cl.
CPC ........ *C12N 15/8257* (2013.01); *C07K 2319/73* (2013.01); *A61K 39/145* (2013.01); *C07K 2319/70* (2013.01); *C12N 2760/16122* (2013.01); *C12N 2760/16134* (2013.01); *C07K 14/005* (2013.01); *C07K 2319/50* (2013.01); *C07K 2319/735* (2013.01)
USPC .................. 424/192.1; 424/210.1; 424/206.1; 435/69.7; 435/69.3; 435/419; 435/91.4; 435/320.1; 800/278; 800/294; 800/288; 536/23.1; 536/23.72

(58) Field of Classification Search
None
See application file for complete search history.

(56) References Cited

U.S. PATENT DOCUMENTS

| | | | |
|---|---|---|---|
| 5,232,833 A | 8/1993 | Sanders et al. | |
| 5,486,510 A | 1/1996 | Bouic et al. | |
| 5,762,939 A | 6/1998 | Smith et al. | |
| 5,858,368 A | 1/1999 | Smith et al. | |
| 6,489,537 B1 | 12/2002 | Rea et al. | |
| 7,125,978 B1 | 10/2006 | Vezina et al. | |
| 7,132,291 B2 | 11/2006 | Cardineau et al. | |
| 7,763,450 B2 | 7/2010 | Robinson et al. | |
| 2001/0006950 A1 | 7/2001 | Punnonen et al. | |
| 2003/0079248 A1 | 4/2003 | Arntzen et al. | |
| 2004/0002061 A1 | 1/2004 | Kawaoka | |
| 2005/0048074 A1 | 3/2005 | Cardineau | |
| 2005/0223430 A1 | 10/2005 | Bakker et al. | |
| 2006/0252132 A1 | 11/2006 | Yang | |
| 2007/0286873 A1 | 12/2007 | Williams et al. | |
| 2008/0008725 A1* | 1/2008 | Weeks-Levy et al. | 424/209.1 |
| 2009/0311669 A1 | 12/2009 | Kawaoka | |
| 2010/0239610 A1 | 9/2010 | D'Aoust et al. | |
| 2010/0310604 A1 | 12/2010 | D'Aoust et al. | |
| 2011/0191915 A1 | 8/2011 | Couture et al. | |
| 2011/0293650 A1 | 12/2011 | D'Aoust et al. | |
| 2012/0189658 A1 | 7/2012 | Couture et al. | |

FOREIGN PATENT DOCUMENTS

| | | |
|---|---|---|
| CA | 2615372 | 1/2009 |
| CA | 2693956 | 1/2009 |
| CA | 2707235 | 6/2009 |
| EP | 2173886 | 6/2013 |
| WO | WO 86/03224 | 6/1986 |
| WO | WO 95/31540 | 11/1995 |
| WO | WO 98/56906 | 12/1998 |
| WO | WO 00/09725 | 2/2000 |
| WO | WO 00/56906 | 9/2000 |
| WO | WO 02/074795 | 9/2002 |

(Continued)

OTHER PUBLICATIONS

Richter et al (Nature Biotechnology, 18, pp. 1167-1171, 2000).*
Weissenhorn et al (Proc. Natl. Acad. Sci., vol. 94, pp. 6065-6069, 1997).*
Twyman et al (Trends in Biotechnology, 21(12), pp. 570-579, 2003).*
Asahi-Ozaki et al (Microbes and Infection, 8, pp. 2706-2714, 2006).*
Hiatt, et al., "Monoclonal antibodies from plants: a new speed record," Proc. Natl. Acad. Sci. U.S.A.(2006) 103, 14645-14646.
Hiatt, A., et al., Production of Antibodies in Transgenic Plants, Nature (1989) 342: 76-78.

(Continued)

Primary Examiner — David T Fox
Assistant Examiner — Stephen Uyeno
(74) Attorney, Agent, or Firm — Kenneth H. Sonnenfeld; King & Spalding LLP

(57) ABSTRACT

The present invention provides a recombinant soluble trimeric hemagglutinin (rHA) protein comprising a hemagglutinin ectodomain and an oligomerization domain. The rHA is produced as a soluble homotrimer, and may further comprises a signal peptide and/or an endoplasmic reticulum (ER) retention signal. The invention is also directed to nucleic acids encoding the rHA of the invention, as well as vectors and chimeric constructs comprising the nucleic acid. Methods of producing the rHA are also provided. The rHA described herein may be used to formulate influenza vaccines, or may be used to enrich existing vaccines.

23 Claims, 14 Drawing Sheets

(56) References Cited

FOREIGN PATENT DOCUMENTS

| WO | WO 03/068163 | 8/2003 |
|---|---|---|
| WO | WO 03/068923 | 8/2003 |
| WO | WO 03/068993 | 8/2003 |
| WO | WO 2004/098530 | 11/2004 |
| WO | WO 2004/098533 | 11/2004 |
| WO | WO 2005/020889 | 3/2005 |
| WO | WO 2006/119516 | 11/2006 |
| WO | WO 2007/011904 | 1/2007 |
| WO | WO 2007/047831 | 4/2007 |
| WO | WO 2007/095318 | 8/2007 |
| WO | WO 2007/130327 | 11/2007 |
| WO | WO 2008/054540 | 5/2008 |
| WO | WO 2008/060669 | 5/2008 |
| WO | WO 2008/151440 | 12/2008 |
| WO | WO 2009/009876 | 1/2009 |
| WO | WO 20091008573 | 1/2009 |
| WO | WO 2009/026397 | 2/2009 |
| WO | WO 2009/076778 | 6/2009 |
| WO | WO 2009/087391 | 7/2009 |
| WO | WO 2010/003225 | 1/2010 |
| WO | WO 2010/006452 | 1/2010 |
| WO | WO 2010/025285 | 3/2010 |
| WO | WO 2010/077712 | 7/2010 |

OTHER PUBLICATIONS

Houston, N., et al., "Phylogenetic Analyses Identify 10 Classes of the Protein Disulfide Isomerase Family in Plants, Including Single-Domain Protein Disulfide Isomerase-Related Proteins," Plant Physiology, 2005, vol. 137, pp. 762-778.
Suzuki, "Sialobiology of Influenza Molecular Mechanism of Host Range Variation of Influenza Viruses," Biol. Pharm. Bull., 28(3), pp. 399-408, 2005.
Vézina, et al., "Transient co-expression for fast and high-yield production of antibodies with human-like N-glycans in plants," *Plant Biotechnology Journal*(2009) 7(5), 442-455.
Medicago Inc, Office Action for Canadian Patent Application 2,693,956 dated Oct. 16, 2012, 2 pages.
Medicago Inc, Office Action for Canadian Patent Application No. 2,707,235 dated Sep. 28 2012, 2 pages.
Medicago Inc., The Second Office Action for Chinese Patent Application No. 200980126670.5 dated Nov. 5, 2012, 16 pages.
Medicago Inc., The Second Office Action for Chinese Patent Application No. 200880107072.9 dated Jul. 24, 2012, 16 pages.
Medicago Inc., The Second Office Action for Chinese Patent Application No. 200980109781.5 dated Nov. 27, 2012, 8 pages.
Medicago Inc., Notification of the First Office Action for Chinese Patent Application No. 200980134868.8 dated Jul. 16, 2012. 10 pages.
Office Action for Eurasian Patent Application No. 201000195/28 dated Jun. 13, 2012, 2 pages.
Office Action for Eurasian Patent Application No. 201001198 dated Aug 28, 2012, 8 pages.
Medicago Inc., Communication pursuant to Article 94(3) EPC for European Patent Application No. EP 08783201.0 dated Oct. 26, 2012, 3 pages.
Medicago Inc., Decision to Grant a European patent pursuant to Article 97(1) EPC for European Patent Application No. 09700061.6 dated Aug. 17, 2012, 1 page.
Medicago Inc., Communication pursuant to Article 94(3) EPC for European Patent Application No. EP 09793751.0 dated Aug. 23, 2012, 10 pages.
Medicago Inc., Office Action for Indonesian Patent Application No. W-0020102481 dated Sep. 18, 2012, 4 pages.
Notification of Defects in Israel Patent Application No. 203018 dated May 8, 2012.
Notification of Defects in Israel Patent Application No. 206967 dated May 9, 2012.
Notification of Defects in Israel Patent Application No. 210215 dated Oct. 25, 2012, 4 pages.
Medicago Inc., New Zealand Patent No. 582360, Letters Patent dated Aug. 6, 2012, 1 page.
Medicago Inc., Examination Report for New Zealand Patent Application No. 587108 dated Mar. 21, 2011, 2 pages.
Medicago Inc., Examination Report for New Zealand Patent Application No. 587108 dated Jun. 27, 2012, 2 pages.
Medicago Inc., Examination Report for New Zealand Patent Application No. 597401Exam Report dated Jul. 9, 2012, 1 page.
Medicago Inc., Notification of Transmittal of International Preliminary Report on Patentability for PCT/CA2011/001228 dated Decmber 4, 2012, 8 pages.
Medicago Inc., Certificate of Grant of Patent for Singapore Patent Application No. 201000090-9 dated Apr. 30, 2012.
D'Aoust et al., Office Action for U.S. Appl. No. 12/669,033 dated Aug. 13, 2012, 8 pages.
D'Aoust et al., Office Action for U.S. Appl. No. 12/669,033 dated Oct. 4, 2012, 33 pages.
D'Aoust et al., Office Action for U.S. Appl. No. 12/863,772 dated Sep. 27, 2012, 9 pages.
D'Aoust et al., Office Action for U.S. Appl. No. 12/863,772 dated Dec. 14, 2012, 28 pages.
Database Genbank, Accession No. FJ966082.1, "Influenza A Virus (A/California/Apr. 2009(H1N1)) Segment 4 Hemagglutinin (HA) gene, Complete CDS," retrieved on Mar. 3, 2012.
Dawood et al., "Emergence of a Novel Swine—Origin Influenza A (H1N1) Virus in Humans," N. Eng. J. Med., 360, pp. 2605-2615, Influenza A Virus.
(A/California/Apr. 2009 H1N1) segment 4 hamegglutinin (HA) gene, Genback Accession FJ966082.
Fischer et al., "Towards molecular farming in the future: moving from diagnostic protein and antibody production in microbes to plants," *Biotechnol. Appl. Biochem.*30: 113-116, 1999.
Hartl, "Molecular chaperones in cellular protein folding," Nature, vol. 381, pp. 571-580, Jun. 13, 1996.
Huang et al., "A DNA Replicon System for Rapid High-Level Production of Virus-Like Particles in Plants," Biotechnolo. Bioeng., vol. 103, No. 4, pp. 706-714, Jul. 1, 2009.
Huang et al., "High-Level Rapid Production of Full-Sized Monoclonal Antibodies in Plants by a Single-Vector DNA Replicon System," Biotechnol. Bioeng., vol. 106, No. 1, pp. 9-17, May 1, 2010.
Marozin et al., "Antigenic and genetic diversity among swine influenza A H1N1 and H1N2 viruses in Europe," Journal of General Virology, 83, 735-745, 2002.
Meshcheryakova et al., "Cowpea Mosaic Virus Chimeric Particles Bearing the Ectodomain of Matrix Protein 2 (M2E) of the Influenza A Virus: Production and characterization," Applied Molecular Biology, 43:685-694, 2009.
Nemchinov et al., "Transient expression of the ectodomain of matrix protein (M2e) of avian influenza A virus in plants," Protein Expression and Purification, 56:153-159, 2007.
Regnard et al., "High Level Protein Expression in Plants Through the Use of a Novel Autonomously Replicating Geminivirus Shuttle Vector," Plant Biotechnology Journal, vol. 8, No. 1, pp. 38-46, Jan. 2010.
Sainsbury et al., "Extremely High-Level and Rapid Transient Protein Production in Plants Without the Use of Viral Replication," Plant Physiology, vol. 148, pp. 1212-1218, Nov. 2008.
Wilson et al., "Core alpa 1,3-fucose is a key part of the epitope recognized by antibodies reacting against plant N-linked oligosaccharides and is present in a wide variety of plant extracts," Glycobiology, vol. 8:7, 651-661, 1998.
Van Ree et al., "Beta (1,2)-Xylose and alpha (1,3)-fucose residues have a strong contribution in IgE binding to plant glycoallergens," Journal of Biological Chemistry, vol. 275:15, 11451-11458, 2000.
Medicago Inc., Office Action for Canadian Patent Application No. 2,693,956, Jan. 26, 2011, 3 pages.
Medicago Inc., Office Action for Canadian Patent Application No. 2,693,956, Jan. 20, 2012, 2 pages.
Medicago Inc., Office Action for Canadian Patent Application No. 2,730,185, Jun. 28, 2011, 5 pages.
Medicago Inc., Office Action for Canadian Patent Application No. 2,730,185, Nov. 30, 2011, 4 pages.
Medicago Inc., Office Action for Canadian Patent Application No. 2,730,185 , Apr. 27, 2012, 2 pages.

(56) References Cited

OTHER PUBLICATIONS

Medicago Inc., Office Action for Canadian Patent Application No. 2,762,042, Feb. 16, 2012, 3 pages.
Medicago Inc., Office Action for Chinese Patent Application No. 200980109781.5, Jan. 21, 2012, 9 pages.
Medicago Inc., Office Action for Chinese Patent Application No. 200980126670.5, Apr. 6, 2012, 16 pages.
Medicago Inc., Office Action for Chinese Patent Application No. 200880107072.9, Sep. 27, 2011, 8 pages.
Medicago Inc., Office Action for Eurasian Patent Application No. 201000195/28, Dec. 13, 2011, 4 pages.
Medicago Inc., Office Action for Egyptian Patent Application No. PCT 1222/2010, Nov. 18, 2011, 10 pages.
Medicago Inc., Supplementary European Search Report for European Patent Application No. 09793741.1, Jul. 26, 2011, 9 pages.
Medicago Inc., Written Opinion and International Search Report for PCT/CA2011/001427 Mar. 20, 2012, 10 pages.
Medicago Inc., Written Opinion and International Search Report for PCT/CA2011/001228 Jan. 18, 2012, 11 pages.
Medicago Inc., Search Report and Written Opinion for Singapore Patent Application No. 201009568-5, Mar. 12, 2012, 20 pages.
Medicago Inc., Office Action for Vietnamese Patent Application No. 1-201200186, Mar. 8, 2011, 1 page.
Chandler, "Influenza Hemagglutinin Expression in *Nicotiana tabacum* and *Nicotiana benthatniana*," M.Sc. Thesis, Baylor University, Waco, Texas. Aug. 2007 [retrieved on Sep. 22, 2008 from the Internet: <https:/fbearJocs.baylor.eJu/bitstreaml21 04/5049! 1 fLee Chandler Masters.pdf>].
Charland N et al., "An Innovative VLP-based Technology to Respond to Global Influenza Vaccine Needs," Poster Abstract, IDSA Seasonal and Pandemic Influenza Meeting, Arlington, Virginia, USA May 18, 2008 [retrieved on Sep. 1, 2009 from the Internet: <URLwww.idsociety.org/WorkArealdownloadasset.aspx?id=11384>].
Chen, et al., "Influenza Virus Hemagglutinin and Neuraminidase, but Not the Matrix Protein, Are Required for Assembly and Budding Plasmid-Derived Virus-Like Particles, " J. Virol., 81(13), pp. 7111-7123, Jul. 2007.
D'Aoust, et al., "Influenza Virus-Like Particles Produced by Transient Expression in *Nicotiana benthatniana* Induce a Protective Immune Response Against a Lethal Viral Challenge in Mice," Plant Biotechnology Journal, 6, pp. 930-940, 2008.
D'Aoust, et al., "The Production of Hemagglutinin-Based Virus-Like Particles in Plants: A Rapid, Efficient and Safe Response to Pandemic Influenza," Plant Biotech J., 8, pp. 607-619, 2010.
Flandorfer, et al., Chimeric Influenza A Viruses with a Functional Influenza B Virus neuraminidase or Hemaggiutinin, J Virol., 77(17), pp. 9116-9123, Sep. 2003.
Garcea, et al., "Virus-like Particles as Vaccines and Vessels for the Delivery of Small Molecules," Current Opinion in Biotechnology, 15, pp. 513-517, 2004.
Garten, et al., "Influenza A virus (A/California/04/2009(H1N1)) segment 4 hemagglutinin (HA) gene, " [Retrieved on Sep. 2, 2009 from NCBI Entrez Nucleotide: <http://www/ncbi.nlm.nih.gove/nuccore/227809829>].
"M.Sativa mRNA for Protein Disulfide Isomerase, " Genbank Accession No. Z11499, 2006 [Retrieved on May 24, 2011 from <http://www.ncbi.nlm.nih.gov/nuxxoew/Z11499.1>].
"Influenza A virus (A/Caledonia/20/99(H1N1)) hemagglutin (HA) gene, " Genbank Accession No. AY289929, 2003.
Grgacic et al., "Virus-Like Particles: Passport to Immune Recognition, " Methods, 40, pp. 60-65, 2006.
Hahn, et al., "Expression of Hemagglutinin-Neuraminidase Protein of Newcastle Disease Virus in Transgenic Tobacco." Plant Biotechnology Reporter, vol. 1, pp. 85-92, Jun. 2007.
Harbury et al., "A Switch Between Two-, Three-, and Four-Strandes Coiled Coils in GCN4 Leucine Zipper Mutants, " Science, 262, pp. 1401-1407, Nov. 26, 1993.
Huang, et al., "Virus-Like Particle Expression and Assembly in Plants: Hepatitis B and Norwalk viruses, " Vaccine, 23, pp. 1851-1858, 2005.
Huang, et al., "Plant-Derived Measles Virus Hemagglutinin Protein Induces Neutralizing Antibodies in Mice, " Vaccine, 19, pp. 2163-2171, 2001.
Kogan, et al., "Supramolecular Properties of the Proline-Rich γ-Zein N-Terminal Domain, " Biophysical J., 83, pp. 1194-1204, Aug. 2002.
Liu, et al., "Agroinfection as a Rapid Method for Propagating Cowpea Mosaic Virus-based Constructs," J. Virol. Methods, 105, pp. 343-348, 2002.
Mason, at al., "Expression of Norwalk Virus Capsid protein in Transgenic Tobacco and Potato and its Oral Immunogenicity in Mice, " Proc. Natl. Acad. Sci. USA, 93, pp, 5335-5340, May 1996.
Mett, et al., "A Plant-Produced Influenza Subunit Vaccine Protects Ferrets Against Virus Challenge, " Influenza and Other Respi. Viruses, 2(1), pp, 33-40, 2008.
Musiychuk, et al., "A launch Vector for the Production of Vaccine Antigens in Plants, " Influenza and Other Respi, Viruses, vol. 1 , pp. 19-25, 2007.
Quan, et al., "Virus-Like Particle Vaccine Induces Protective Immunity Against Homologous and Heterologous Strains of Influenza Virus, " J Virol., 81(7), pp. 3514-3524, Apr. 2007.
Russell, et al., "H1 and H7 Influenza Haemagglutinin Structures Extend a Structural Classification of Haemagglutinin Subtypes, " Virology, 325, pp. 287- 296, 2004.
Saelens, et al., "Protection of Mice Against a Lethal Influenza Virus Challenge after immunization with Yeast-Derived Secreted Influenza Virus Hemaggiutinin," Eur, J. Biochem., 260, pp. 166-75. 1999.
Schillberg, et al., "Molecular Farming of Recombinant Antibodies in Plants," Cell, Moi. Life Sci., vol. 60, pp. 433-445, 2003.
Shoji, et al., "Plant-Expressed HA as a Seasonal Influenza Vaccine Candidate," Vaccine, 26, pp. 2930-2934, 2008.
Strelkov, et al., "Preliminary Crystallographic Studies of Bacteriophage T4 Fibritin Confirm a Trimeric Coiled-Coil Structure," Virology, 219, pp. 190-194,1996.
Treanor, et. al., "Safety and Immunogenicity of a Baculovirus-Expressed hemagglutinin Influenza Vaccine, A randomized control trial, " JAMA, 297(14), pp. 1577-1582, Apr. 11, 2007.
Wei, et al., "Comparative Efficacy of Neutralizing Antibodies Elicited by Recombinant Hemagglutinin Proteins from Avian H5N1 Influenza Virus, " J Virol., 82(13), pp. 6200-6208, Jul. 2008.
International Search Report and Written Opinion of the International Searching Authority for PCT/CA2009/000941 dated Sep. 10, 2009.
International Preliminary Report on Patentability for PCT/CA2009/000941 dated Jan. 11, 2011.
International Preliminary Report on Patentability for PCT/CA2008/001281 dated Nov. 12, 2009.
International Search Report and Written Opinion of the International Searching Authority for PCT/CA2008/001281 dated Oct. 7, 2008.
International Search Report and Written Opinion of the International Searching Authority for PCT/CA2009/000032 dated Apr. 30, 2009.
International Preliminary Report on Patentability for PCT/CA2009/000032 dated Jul. 27, 2010.
International Search Report and Written Opinion of the International Searching Authority for PCT/CA2009/000926 dated Oct. 1, 2009.
International Preliminary Report on Patentability (Chapter II) for PCT/CA2009/000926 dated Nov. 5, 2010.
International Search Report and Written Opinion of the International Searching Authority for PCT/CA2010/000983 dated Sep. 14, 2010.
Air, "Sequence Relationships Among the Hemagglutinin Genes of 12 Subtypes of Influenza A Virus," Proc. Natl. Acad., vol. 78, No. 12, Dec. 1981, pp. 7639-7643.
Arntzen et al., "Plant-Derived Vaccines and Antibodies: Potential and Limitations," Vaccine, 23, 2005, pp. 1753-1756.
Bao et al., "The Influenza Virus Resource at the National Center for Biotechnology Information," Journal of Virology, vol. 82, No. 2, Jan. 2008, pp. 596-601.
Berger et al., Plant Sterols: Factors Affecting Their Efficacy and Safety as Functional Food Ingredients, Lipids in Health and Disease, 3, 2004, pp. 1-19.
Berman et al., "Announcing the Worldwide Protein Data Bank," Nature Structural Biology, 10: 980, 2003.

(56) References Cited

OTHER PUBLICATIONS

Borisjuk et al., "Expression of Avian Flu Antigen for Bird Immunization," Abstract, Plant Biology & Botany, Retrieved from Internet Site http://2007.botanyconference.org/engine/search/index.php?func=detail&aid=1410 on Sep. 7, 2007, 2 pages total.
Bouic, "Sterols and Sterolins: New Drugs for the Immune System?," Therapeutic Focus, DDT vol. 7, No. 14, Jul. 14, 2002, pp. 775-778.
Bouic, "The Role of Phytosterols and Phytosterolins in Immune Modulation: A Review of the Past 10 Years," Current Opinion in Clinical Nutrition and Metabolic Care, 4, 2001, pp. 471-475.
Bouic et al., "Plant Sterols and Sterolins: A Review of Their Immune-Modulating Properties," Alternative Medicine Review, vol. 4, No. 3, 1999, pp. 170-177.
Brigneti et al., "Viral Pathogenicity Determinants Are Suppressors of Transgene Silencing in *Nicotiana Benthamiana*," The EMBO Journal, vol. 17, No. 22 1998, pp. 6739-6746.
Chandrasekaran et al, "Glycan Topology Determines Human Adaptation of Avian H5N1 Virus Hemagglutinin," Nature Biotechnology, vol. 26, No. 1, Jan. 2008, pp. 107-113.
Chen et al., "Stabilizing the Glycosylation Pattern of Influenza B Hemagglutinin Following Adaptation to Growth in Eggs," Vaccine, vol. 26, 2008, pp. 361-371.
Chiba et al, "Diverse Suppressors of RNA Silencing Enhance Agroinfection by a Viral Replicon," Virology, 346, 2006, pp. 7-14.
Crawford, "Baculovirus-Derived Hemagglutinin Vaccines Protect Against Lethal Influenza Infections by Avian H5 and H7 Subtypes," Vaccine, 17, 1999, pp. 2265-2274.
Cross et al., "Studies on Influenza Haemagglutinin Fusion Peptide Mutants Generated by Reverse Genetics," The EMBO Journal, vol. 20, No. 16, 2001, pp. 4432-4442.
Diaz-Vivancos et al., "The Apoplastic Antioxidant System in Prunus: Response to Long-Term Plum Pox Virus Infection," Journal of Experimental Botany, vol. 57, No. 14, 2006, pp. 3813-3824.
Fischer et al., "Affinity-Purification of a TMV-specific Recombinant Full-Size Antibody from a Transgenic Tobacco Suspension Culture," *J Immunol. Methods*, vol. 226, pp. 1-10, 1999.
Frugis et al., "MsJ1, an alfalfa DnaJ-like gene, is Tissue-Specific and Transcriptionally Regulated During Cell Cycle," Plant Molecular Biology, 40, 1999, pp. 397-408.
Galarza et al., "Virus-Like Particle (VLP) Vaccine Conferred Complete Protection against a Lethal Influenza Virus Challenge," Viral Immunology, vol. 18, No. 1, 2005, pp. 244-251.
Gallagher et al., "Addition of Carbohydrate Side Chains at Novel Sites on Influenza Virus Hemagglutinin Can Modulate the Folding, Transport, and Activity of the Molecule," the Journal of Cell Biology, vol. 107, No. 6, Part 1, Dec. 1988, pp. 2059-2073.
Gallagher et al., "Glycosylation Requirements for Intracellular Transport and Function of the Hemagglutinin of Influenza Virus," Journal of Virology, vol. 66, No. 12, Dec. 1992, pp. 7136-7145.
Gamblin et al., "The Structure and Receptor Binding Properties of the 1918 Influenza Hemagglutinin," Science, vol. 303, Mar. 19, 2004, pp. 1838-1842.
Gillim-Ross et al., "Emerging Respiratory Viruses: Challenges and Vaccine Strategies," Clinical Microbiology Reviews, vol. 19, No. 4, Oct. 2006, pp. 614-636.
Gómez-Puertas, "Efficient Formation of Influenza Virus-Like Particles: Dependence on the Expression Levels of Viral Proteins," Journal of General Virology, 80, 1999, pp. 1635-1645.
Gómez-Puertas, "Influenza Virus Matrix Protein Is the Major Driving Force in Virus Budding," Journal of Virology, vol. 74, No. 24, Dec. 2000, pp. 11538-11547.
Gupta et al., "O-Glycbase version 4.0: a Revised Database of 0-glycosylated Proteins," Nucleic Acids Research, vol. 27, No. 1, 1999, pp. 370-372.
Hamilton et al., "Two Classes of Short Interfering RNA in RNA Silencing," The EMBO Journal, vol. 21, No. 17, 2002, pp. 4671-4679.
Ito et al., "Receptor Specificity of Influenza a Viruses Correlates with the Agglutination of Erythrocytes from Different Animal Species," Virology, 227, 1997, pp. 493-499.
Johansson et al., "Immunization With Influenza A Virus Hemagglutinin and Neuraminidase Produced in Recombinant Baculovirus Results in a Balanced and Broadened Immune Response Superior to Conventional Vaccine," Vaccine 17, 1999, pp. 2073-2080.
Knossow et al., "Variation and Infectivity Neutralization in Influenza," Immunology, 119, 2006, pp. 1-7.
Latham et al., "Formation of Wild-Type and Chimeric Influenza Virus-Like Particles following Simultaneous Expression of Only Four Structural Proteins," Journal of Virology, vol. 75, No. 13, Jul. 2001, pp. 6154-6165.
Lefebvre et al., "Characterization of Lipid Rafts from Medicago truncatula Root Plasma Membranes: A Proteomic Study Reveals the Presence of a Raft-Associated Redox System," Plant Physiology, vol. 144, May 2007, pp. 402-418.
Lin et al., "Genomic Analysis of the Hsp70 Superfamily in *Arabidopsis thaliana*," Cell Stress & Chaperones, 6 (3), 2001, pp. 201-208.
Low et al., "Future of Antibody Purification," Journal of Chromatography B, 848, 2007, pp. 48-63.
Macala et al., "Analysis of Brain Lipids by High Performance Thin-Layer Chromatography and Densitometry," Journal of Lipid Research, vol. 24, 1983, pp. 1243-1250.
Macario, "Heat-Shock Proteins and Molecular Chaperones: Implications for Pathogenesis, Diagnostics, and Therapeutics," Int J Clin Lab, 25, 1995, pp. 59-70.
Mansour et al., "Plasma Membrane Lipid Alterations Induced by NaCl in Winter Wheat Roots," Physiologia Plantarum, 92, 1994, pp. 473-478.
McCauley et al., "Structure and Function of the Influenza Virus Genome," Biochem. J., vol. 211, 1983, pp. 281-294.
Medeiros et al., "Hemagglutinin Residues of Recent Human A(H3N2) Influenza Viruses That Contribute to the Inability to Agglutinate Chicken Erythrocytes," Virology, 289, 2001, pp. 74-85.
Mena et al., "Rescue of a Synthetic Chloramphenicol Acetyltransferase RNA into Influenza Virus-Like Particles Obtained from Recombinant Plasmids," Journal of Virology, vol. 70, No. 8, Aug. 1996, pp. 5016-5024.
Mongrand et al., "Lipid Rafts in Higher Plant Cells," The Journal of Biological Chemistry, vol. 279, No. 35, 2004, pp. 36277-36286.
Musiychuk et al., "A Launch Vector for the Production of Vaccine Antigens in Plants," Influenza and Other Respiratory Viruses, 1, 2006, pp. 19-25.
Nakahara et al, "Glycoconjugate Data Bank: Structures: an Annotated Glycan Structure Database and N-glycan Primary Structure Verification Service," Nucleic Acids Research, vol. 36, 2008, pp. D368-D371.
Neumann et al., "Plasmid-Driven Formation of Influenza Virus-Like Particles," Journal of Virology, vol. 74, No. 1, Jan. 2000, pp. 547-551.
Nuttall et al., "ER-Resident Chaperone Interactions With Recombinant Antibodies in Transgenic Plants," Eur. J. Biochem., 269, 2002, pp. 6042-6051.
Olsen et al., "Immunogenicity and Efficacy of Baculovirus-Expressed and DNA-Based Equine Influenza Virus Hemagglutinin Vaccines in Mice," Vaccine, vol. 15, No. 10, 1997, pp. 1149-1156.
Parsell et al., "The Function of Heat-Shock Proteins in Stress Tolerance: Degradation and Reactivation of Damaged Proteins," Annu. Rev. Gent., 27, 1993, pp. 437-496.
Plotkin et al., "Hemagglutinin Sequence Clusters and the Antigenic Evolution of Influenza A Virus," PNAS, vol. 99, No. 9, Apr. 30, 2002, pp. 6263-6268.
Pushko et al., "Influenza Virus-Like Particles Comprised of the HA, NA, and MI Proteins of H9N2 Influenza Virus Induce Protective Immune Responses in BALB/c Mice," Vaccine, 23, 2005, pp. 5751-5759.
Pwee et al., "The Pea Plastocyanin Promoter Directs Cell-Specific But Not Full Light-Regulated Expression in Transgenic Tobacco Plants," The Plant Journal, 3(3), 1993, pp. 437-449.
Rowe et al., "Detection of Antibody to Avian Influenza a (H5N1) Virus in Human Serum by Using a Combination of Serologi Assays," Journal of Clinical Microbiology, vol. 37, No. 4, pp. 937-943, Apr. 1999.
Roy et al., "Virus-like particles as a vaccine delivery system," Human Vaccines, 4:1, Jan./Feb. 2008, pp. 5-12.

(56) References Cited

OTHER PUBLICATIONS

Sainsbury et al., "Expression of Multiple Proteins Using Full-Length and Deleted Versions of Cowpea Mosaic Virus RNA-2," Plant Biotechnology Journal, 6, 2008, pp. 82-92.
Sainsbury et al., "Extremely High-Level and Rapid Transient Protein Production in Plants without the Use of Viral Replication," Plant Physiology, vol. 148, Nov. 2008, pp. 1212-1218.
Saint-Jore-Dupas et al., "From Planta to Pharma with Glycosylation in the Toolbox," Trends in Biotechnology 25(7), pp. 317-323, 2007.
Salzberg et al., "Genome Analysis Linking Recent European and African Influenza (H5N1) Viruses," Emerging Infectious Diseases, CDC, vol. 13, No. 5, May 2007, pp. 713-718.
Schillberg et al., "Apoplastic and Cytosolic Expression of Full-Size Antibodies and Antibody Fragments in *Nicotiana Tabacum*," Transgenic Res., vol. 8, 1999, pp. 255-263.
Skehel et al., "Receptor Binding and Membrane Fusion in Virus Entry: The Influenza Hemagglutinin," Annu. Rev. Biochem., 69, 2000, pp. 531-569.
Staehelin, "The plant ER: a Dynamic Organelle Composed of a Large Number of Discrete Functional Domains," The Plant Journal, 11(6), 1997, pp. 1151-1165.
Toukach et al., "Sharing of worldwide distributed carbohydrate-related digital resources: online connection of the Bacterial Carbohydrate Structure DataBase and Glycosciences.de," Nucleic Acids Research, vol. 35, 2007, pp. D280-D286.
Vaccaro et al., "Plasticity of Influenza Haemagglutinin Fusion Peptides and Their Interaction with Lipid Bilayers," Biophysical Journal, vol. 88, Jan. 2005, pp. 2536.
Wagner et al., "Interpendence of Hemagglutinin Glycosylation and Neuramindase as Regulators of Influenza Virus Growth: a Study by Reverse Genetics," Journal of Virology, vol. 74, No. 14, Jul. 2000, pp. 6316-6323.
Wakefield et al., "RNA-Binding Properties of Influenza A Virus Matrix Protein M1," Nucleic Acids Research, vol. 17, No. 21, 1989, pp. 8569-8580.
Wang et al., "Expression and Purification of an Influenza Hemagglutinin-One Step Closer to a Recombinant Protein-Based Influenza Vaccine," Vaccine, 24, 2006, pp. 2176-2185.
Weldon et al., "Enhanced Immunogenicity of Stabilized Trimeric Soluble Influenza Hemagglutinin," PLoS ONE, vol. 5, Issue 9, e12466, Sep. 2010, pp. 1-8.
Medicago, Inc., European Search Report from European Application No. 08783201.0 dated Sep. 13, 2010, 9 pages total.
Medicago, Inc., Examination Report dated Nov. 8, 2010 for New Zealand Application No. 582360, 9 pages total.
Medicago, Inc., Examination Report dated Apr. 15, 2011 for New Zealand Application No. 590144, 3 pages total.
Medicago, Inc., Canadian Office Action dated Jun. 1, 2011 for Canadian Application No. 2,707,235, 5 pages total.
Medicago, Inc., Canadian Office Action dated Sep. 22, 2011 for Canadian Application No. 2,693,956, 3 pages total.
Medicago, Inc., Canadian Office Action dated Oct. 28, 2011 for Canadian Application No. 2,707,235, 3 pages total.
Medicago, Inc., Communication Pursuant to Article 94(3) EPC from corresponding European Application No. 08 783 201.0 dated May 26, 2011, 4 pages total.
Medicago, Inc., Supplementary European Search Report from European Application No. 09793751.0 dated Sep. 28, 2011, 11 pages total.
Medicago, Inc., Supplementary European Search Report from European Application No. 09700061.6 dated Mar. 7, 2011, 11 pages total.
Medicago, Inc., Written Opinion, Search Report and Examination Report for Singapore Application No. 201000090-9 dated May 2, 2011, 16 pages total.
Kobayashi, Y. et al., "Chaperones Hsp70 and Hsp40 Suppress Aggregate Formation and Apoptosis in cultured Neuronal Cells Expressing Truncated Androgen Receptor Protein with Expanded Polyglutamine Tract," the Journal of Biological Chemistry, 275(12), pp. 8772-8778, 2000.
Liu, L., et al., "Cowpea mosaic virus-based systems for th eproduction of antigens and antibodies in plants," Vaccine 23, pp. 1788-1792, 2005.
Ma, Julian K-C., et al., "The Production of Recombinant Pharmaceutical Proteins in Plants," Nature 2003, vol. 4, pp. 794-805, 2003.
Rivard, D., et al., "An in-built proteinase inhibitor system for the protection of recombinant proteins recovered from transgenic plants," Plant Biotechnology Journal, 4, pp. 359-368, 2006.
Spitsin, S. et al., "Immunological assessment of plant-derived avian flu H5/HA1 variants," Vaccine, 27, pp. 1289-1292, 2009.
Whitelam, G., "The Production of Recombinant Proteins in Plants," J Sci Food Agric, 68, pp. 1-9, 1995.
Medicago Inc., Notice of Allowance dated Aug. 14, 2013 for Canadian patent application CA 2,707,235, 1 page.
Medicago Inc., Office Action dated Jul. 23, 2013 for Chinese application CN 200980126670.5 together with English translation, 14 pages.
Medicago Inc., Office Action dated Aug. 27, 2013 for Egyptian application EG PCT 61/2010 with English translation, 12 pages.
Medicago Inc., Examination Report dated Aug. 1, 2013 for European application 09793751.0, 7 pages.
Medicago Inc., Office Action dated Jul. 17, 2013 for Japanese Application JP 2010-516334 with English translation, 8 pages.
Medicago Inc., English translation of Office Action dated Aug. 30, 2013 for Japanese application JP 2010-542486, 16 pages.
Medicago Inc., Office Action dated Aug. 7, 2013 for Korean application KR 10- 2012-7001798 with English translation, 6 pages.
Medicago Inc., Office Action dated Sep. 12, 2013 for U.S. Appl. No. 13/748,531, 47 pages.
Medicago Inc., Office Action dated Jul. 17, 2013 re U.S. Appl. No. 13/003,570, 33 pages.
Medicago Inc., Office Action for Chinese application CN 200980134868.8, dated Jan. 15, 2013, 16 pages.
Medicago Inc., Office Action for Mexican application MX/a/2010/000525, dated Mar. 6, 2013, 5 pages.
Medicago Inc., Office Action for Mexican application MX/a/2010/007962, dated Mar. 6, 2013, 7 pages.
Medicago Inc., Office Action for Mexican application MX/a/2011/000459, dated Mar. 6, 2013, 6 pages.
Medicago Inc., Further Examination Report for New Zealand application 587108, dated Jan. 28, 2013, 2 pages.
Medicago Inc., Office Action for Thailand application 1101003761, dated Mar. 13, 2013, 4 pages.
Medicago Inc., Restriction Requirement for U.S. Appl. No. 13/748,531, dated Mar. 25, 2013, 9 pages.
Garten, et al., "Emergence of a Novel Swine—Origin Influenza a (H1N1) Virus in Humans," New England Journal of Medicine, Jun. 2009, vol. 360, No. 25, pp. 2605-2615.
Li, et al., "Influenza A Virus Transfectants with Chimeric Hemagglutinins Containing Epitopes from Different Subtypes," Journal of Virology, vol. 66, No. 3, 1992, pp. 399-404.
Mori, et al., "A Novel amino acid substitution at the receptor-binding site on the hemagglutinin of H3N2 influenza A viruses isolated from 6 cases with acute encephalopathy during the 1997-1998 season in Tokyo," Arch. Virol., 1999, vol. 144, pp. 147-155.
Nobusawa, "Protective antigen of influenza virus," Dept. Of Virology, Nippon Rinsho, vol. 55(1), 1997, pp. 2719-2724, English Abstract.
Shorrosh, et al., "Sequence analysis and developmental expression of an alfalfa protein disulfide isomerase," Plant Molecular Biology, vol. 19, pp. 319-321, 1992.
Yang, et al. "Immunization by Avian H5 Influenza Hemagglutinin Mutants with Altered Receptor Binding Specificity," Science, vol. 317, Aug. 2007, pp. 825-828.
Medicago Inc., Office Action for Australian application AU2008278222, dated May 21, 2013, 3 pages.
Medicago Inc., Office Action for Australian application AU 2009202819, dated Jun. 13, 2013, 3 pages.
Medicago Inc., Office Action for Canadian application CA 2,693,956, dated Mar. 1, 2013, 2 pages.
Medicago Inc., Office Action for Chinese application 200980134868.8, dated May 30, 2013, 8 pages.

(56) References Cited

OTHER PUBLICATIONS

Medicago Inc., Office Action for Chinese application CN 201080035066.4, dated Jun. 28, 2013, 8 pages.
Medicago Inc., Office Action for Eurasian application EA 201001198, dated Apr. 24, 2013, 3 pages.
Medicago Inc. Decision to Grant for European application EP08783201.0, 1 page, May 31, 2013.
Medicago Inc. Office Action for Indonesian application W-0020102481, dated May 10, 2013, 4 pages.
Medicago Inc. Office Action for Japanese application JP 2012-516452, dated May 28, 2013, 3 pages.
Medicago Inc. Office Action for Russian application RU2011105073/10, dated Apr. 5, 2013, 9 pages.
Garten, et al., "Antigenic and Genetic Characteristics of Swine-Origin 2009 A(H1N1) Influenza Viruses Circulating in Humans," Science, vol. 325, pp: 197-201, 2009.
Medicago Inc., Extended Search Report for European application 12181077.4 dated Feb. 15, 2013, 8 pages.
Medicago Inc., Office Action for Canadian application CA 2,707,235, dated Mar. 1, 2013, 2 pages.
Medicago Inc., Office Action for Chinese application CN 200980126670.5, dated Mar. 15, 2013, 14 pages.
Medicago Inc., Office Action for Chinese application CN 200880107072.9, dated Feb. 21, 2013, 6 pages.

* cited by examiner

LKQIEDKIEEILSKIYHIENEIARIKKLIGESAA   (SEQ ID NO :1)

Fig. 2

```
1      M   A   K   N   V   A   I   F   G   L   L   F   S   L
1    5'-ATG GCG AAA AAC GTT GCG ATT TTC GGT TTA TTG TTT TCT CTT

15     L   V   L   V   P   S   Q   I   F   A              SEQ ID NO:6
43     CTT CTG TTG GTT CCT TCT CAG ATC TTC GCT -3'         SEQ ID NO:7
```

Fig. 3

| | | | | | |
|---|---|---|---|---|---|
| 1 | *MKAKLLVLLC* | *TFTATYADTI* | CIGYHANNST | DTVDTVLEKN | VTVTHSVNLL EDSHNGKLCL |
| 61 | LKGIAPLQLG | NCSVAGWILG | NPECELLISK | ESWSYIVETP | NPENGTCYPG YFADYEELRE |
| 121 | QLSSVSSFER | FEIFPKESSW | PNHTVTGVSA | SCSHNGKSSF | YRNLLWLTGK NGLYPNLSKS |
| 181 | YVNNKEKEVL | VLWGVHHPPN | IGNQRALYHT | ENAYVSVVSS | HYSRRFTPEI AKRPKVRDQE |
| 241 | GRINYYWTLL | EPGDTIIFEA | NGNLIAPWYA | FALSRGFGSG | IITSNAPMDE CDAKCQTPQG |
| 301 | AINSSLPFQN | VHPVTIGECP | KYVRSAKLRM | VTGLRNIPSI | QS<u>RGLFGAIA GFIEGGWTGM</u> |
| 361 | <u>VDGWYGYHHQ</u> | NEQGSGYAAD | QKSTQNAING | ITNKVNSVIE | KMNTQFTAVG KEFNKLERRM |
| 421 | ENLNKKVDDG | FLDIWTYNAE | LLVLLENERT | LDFHDSNVKN | LYEKVKSQLK NNAKEIGNGC |
| 481 | FEFYHKCNNE | CMESVKNGTY | DYPKYSEESK | LNREKIDGVK | LESMGVYQIL AIYSTVASS |
| 541 | VLLVSLGAIS | FWMCSNGSLQ | CRICI | | SEQ ID NO:8 |

Fig. 4

```
 -7    MAKNVAIFGL LFSLL VLVPS QIFADTICIG YHANNSTDTVDTVLEKNVTVTHSVNLLEDSHN
 54    GKLCLLKGIA PLQLGNCSVA GWILGNPECE LLISKESWSY IVETPNPENG TCYPGYFADY
114    EELREQLSSV SSFERFEIFP KESSWPNHTV TGVSASCSHN GKSSFYRNLL WLTGKNGLYP
174    NLSKSYVNNK EKEVLVLWGV HHPPNIGNQR ALYHTENAYV SVVSSHYSRR FTPEIAKRPK
234    VRDQEGRINY YWTLLEPGDT IIFEANGNLI APWYAFALSR GFGSGIITSN APMDECDAKC
294    QTPQGAINSS LPFQNVHPVT IGECPKYVRS AKLRMVTGLR NIPSIQSRGL FGAIAGFIEG
354    GWTGMVDGWY GYHHQNEQGS GYAADQKSTQ NAINGITNKV NSVIEKMNTQ FTAVGKEFNK
414    LERRMENLNK KVDDGFLDIW TYNAELLVLL ENERTLDFHD SNVKNLYEKV KSQLKNNAKE
474    IGNGCFEFYH KCNNECMESV KNGTYDYPKY SEESKLNREK IDGVKLESMG VYQIL AIYS
534    TVASSLVLLV SLGAISFWMC SNGSLQCRIC I*      SEQ ID NO:9
```

Fig. 5A

```
 -7    MAKNVAIFGL LFSLL VLVPS QIFADTICIG YHANNSTDTVDTVLEKNVTVTHSVNLLEDSHN
 54    GKLCLLKGIA PLQLGNCSVA GWILGNPECE LLISKESWSY IVETPNPENG TCYPGYFADY
114    EELREQLSSV SSFERFEIFP KESSWPNHTV TGVSASCSHN GKSSFYRNLL WLTGKNGLYP
174    NLSKSYVNNK EKEVLVLWGV HHPPNIGNQR ALYHTENAYV SVVSSHYSRR FTPEIAKRPK
234    VRDQEGRINY YWTLLEPGDT IIFEANGNLI APWYAFALSR GFGSGIITSN APMDECDAKC
294    QTPQGAINSS LPFQNVHPVT IGECPKYVRS AKLRMVTGLR NIPSIQSRGL FGAIAGFIEG
354    GWTGMVDGWY GYHHQNEQGS GYAADQKSTQ NAINGITNKV NSVIEKMNTQ FTAVGKEFNK
414    LERRMENLNK KVDDGFLDIW TYNAELLVLL ENERTLDFHD SNVKNLYEKV KSQLKNNAKE
474    IGNGCFEFYH KCNNECMESV KNGTYDYPKY SEESKLNREK IDGVKLESMG VYSEKDEI*
       SEQ ID NO:10
```

Fig. 5B

```
 -7    MAKNVAIFGL LFSLL VLVPS QIFADTICIG YHANNSTDTVDTVLEKNVTVTHSVNLLEDSHN
 54    GKLCLLKGIA PLQLGNCSVA GWILGNPECE LLISKESWSY IVETPNPENG TCYPGYFADY
114    EELREQLSSV SSFERFEIFP KESSWPNHTV TGVSASCSHN GKSSFYRNLL WLTGKNGLYP
174    NLSKSYVNNK EKEVLVLWGV HHPPNIGNQR ALYHTENAYV SVVSSHYSRR FTPEIAKRPK
234    VRDQEGRINY YWTLLEPGDT IIFEANGNLI APWYAFALSR GFGSGIITSN APMDECDAKC
294    QTPQGAINSS LPFQNVHPVT IGECPKYVRS AKLRMVTGLR NIPSIQSRGL FGAIAGFIEG
354    GWTGMVDGWY GYHHQNEQGS GYAADQKSTQ NAINGITNKV NSVIEKMNTQ FTAVGKEFNK
414    LERRMENLNK KVDDGFLDIW TYNAELLVLL ENERTLDFHD SNVKNLYEKV KSQLKNNAKE
474    IGNGCFEFYH KCNNECMESV KNGTYDYPKY SEESKLNREK IDGVKLESMG VYHDEI*
       SEQ ID NO:11
```

Fig. 5C

```
 -7    MAKNVAIFGL LFSLL VLVPS QIFADTICIG YHANNSTDTVDTVLEKNVTVTHSVNLLEDSHN
 54    GKLCLLKGIA PLQLGNCSVA GWILGNPECE LLISKESWSY IVETPNPENG TCYPGYFADY
114    EELREQLSSV SSFERFEIFP KESSWPNHTV TGVSASCSHN GKSSFYRNLL WLTGKNGLYP
174    NLSKSYVNNK EKEVLVLWGV HHPPNIGNQR ALYHTENAYV SVVSSHYSRR FTPEIAKRPK
234    VRDQEGRINY YWTLLEPGDT IIFEANGNLI APWYAFALSR GFGSGIITSN APMDECDAKC
294    QTPQGAINSS LPFQNVHPVT IGECPKYVRS AKLRMVTGLR NIPSIQSRGL FGAIAGFIEG
354    GWTGMVDGWY GYHHQNEQGS GYAADQKSTQ NAINGITNKV NSVIEKMNTQ FTAVGKEFNK
414    LERRMENLNK KVDDGFLDIW TYNAELLVLL ENERTLDFHD SNVKNLYEKV KSQLKNNAKE
474    IGNGCFEFYH KCNNECMESV KNGTYDYPKY SEESKLNREK IDGVKLESMG VY*
       SEQ ID NO:12
```

Fig. 5D

```
 -7    MAKNVAIFGL LFSLL VLVPS QIFADTICIG YHANNSTDTVDTVLEKNVTVTHSVNLLEDSHN
 54    GKLCLLKGIA PLQLGNCSVA GWILGNPECE LLISKESWSY IVETPNPENG TCYPGYFADY
114    EELREQLSSV SSFERFEIFP KESSWPNHTV TGVSASCSHN GKSSFYRNLL WLTGKNGLYP
174    NLSKSYVNNK EKEVLVLWGV HHPPNIGNQR ALYHTENAYV SVVSSHYSRR FTPEIAKRPK
234    VRDQEGRINY YWTLLEPGDT IIFEANGNLI APWYAFALSR GFGSGIITSN APMDECDAKC
294    QTPQGAINSS LPFQNVHPVT IGECPKYVRS AKLRMVTGLR NIPSIQSRGL FGAIAGFIEG
354    GWTGMVDGWY GYHHQNEQGS GYAADQKSTQ NAINGITNKV NSVIEKMNTQ FTAVGKEFNK
414    LERRMENLNK KVDDGFLDIW TYNAELLVLL ENERTLDFHD SNVKNLYEKV KSQLKNNAKE
474    IGNGCFEFYH KCNNECMESV KNGTYDYPKY SEESKLNREK IDGVKLESMG VYLKQIEDKI
527    EEILSKIYHI ENEIARIKKL IGESAA*      SEQ ID NO:13
```

Fig. 5E

```
 -7    MAKNVAIFGL LFSLL VLVPS QIFADTICIG YHANNSTDTVDTVLEKNVTVTHSVNLLEDSHN
 54    GKLCLLKGIA PLQLGNCSVA GWILGNPECE LLISKESWSY IVETPNPENG TCYPGYFADY
114    EELREQLSSV SSFERFEIFP KESSWPNHTV TGVSASCSHN GKSSFYRNLL WLTGKNGLYP
174    NLSKSYVNNK EKEVLVLWGV HHPPNIGNQR ALYHTENAYV SVVSSHYSRR FTPEIAKRPK
234    VRDQEGRINY YWTLLEPGDT IIFEANGNLI APWYAFALSR GFGSGIITSN APMDECDAKC
294    QTPQGAINSS LPFQNVHPVT IGECPKYVRS AKLRMVTGLR NIPSIQSRGL FGAIAGFIEG
354    GWTGMVDGWY GYHHQNEQGS GYAADQKSTQ NAINGITNKV NSVIEKMNTQ FTAVGKEFNK
414    LERRMENLNK KVDDGFLDIW TYNAELLVLL ENERTLDFHD SNVKNLYEKV KSQLKNNAKE
474    IGNGCFEFYH KCNNECMESV KNGTYDYPKY SEESKLNREK IDGVKLESMG VYLKQIEDKI
527    EEILSKIYHI ENEIARIKKL IGESAASEDK EL*    SEQ ID NO:14
```

Fig. 5F

```
 -7   MAKNVAIFGL LFSLL VLVPS QIFADTICIG YHANNSTDTVDTVLEKNVTVTHSVNLLEDSHN
 54   GKLCLLKGIA PLQLGNCSVA GWILGNPECE LLISKESWSY IVETPNPENG TCYPGYFADY
114   EELREQLSSV SSFERFEIFP KESSWPNHTV TGVSASCSHN GKSSFYRNLL WLTGKNGLYP
174   NLSKSYVNNK EKEVLVLWGV HHPPNIGNQR ALYHTENAYV SVVSSHYSRR FTPEIAKRPK
234   VRDQEGRINY YWTLLEPGDT IIFEANGNLI APWYAFALSR GFGSGIITSN APMDECDAKC
294   QTPQGAINSS LPFQNVHPVT IGECPKYVRS AKLRMVTGLR NIPSIQSRGL FGAIAGFIEG
354   GWTGMVDGWY GYHHQNEQGS GYAADQKSTQ NAINGITNKV NSVIEKMNTQ FTAVGKEFNK
414   LERRMENLNK KVDDGFLDIW TYNAELLVLL ENERTLDFHD SNVKNLYEKV KSQLKNNAKE
474   IGNGCFEFYH KCNNECMESV KNGTYDYPKY SEESKLNREK IDGVKLESMG VYGGAGPPP
527   VHLPPPVHLP PPVHLPPPVH LPPPVHLPPP VHLPPPVHLP PPVHLPPPSA  *
      SEQ ID NO:15
```

Fig. 5G

```
 -7   MAKNVAIFGL LFSLL VLVPS QIFADTICIG YHANNSTDTVDTVLEKNVTVTHSVNLLEDSHN
 54   GKLCLLKGIA PLQLGNCSVA GWILGNPECE LLISKESWSY IVETPNPENG TCYPGYFADY
114   EELREQLSSV SSFERFEIFP KESSWPNHTV TGVSASCSHN GKSSFYRNLL WLTGKNGLYP
174   NLSKSYVNNK EKEVLVLWGV HHPPNIGNQR ALYHTENAYV SVVSSHYSRR FTPEIAKRPK
234   VRDQEGRINY YWTLLEPGDT IIFEANGNLI APWYAFALSR GFGSGIITSN APMDECDAKC
294   QTPQGAINSS LPFQNVHPVT IGECPKYVRS AKLRMVTGLR NIPSIQSRGL FGAIAGFIEG
354   GWTGMVDGWY GYHHQNEQGS GYAADQKSTQ NAINGITNKV NSVIEKMNTQ FTAVGKEFNK
414   LERRMENLNK KVDDGFLDIW TYNAELLVLL ENERTLDFHD SNVKNLYEKV KSQLKNNAKE
474   IGNGCFEFYH KCNNECMESV KNGTYDYPKY SEESKLNREK IDGVKLESMG VYGGAGPPP
527   VHLPPPVHLP PPVHLPPPVH LPPPVHLPPP VHLPPPVHLP PPVHLPPPSA  SEKDEL*
      SEQ ID NO:16
```

Fig. 5H

| | |
|---|---|
| 1 | gggcccATGG CGAAAAACGT TGCGATTTTC GGTTTATTGT TTTCTCTTCT TCTGTTGGTT |
| 61 | CCTTCTCAGA TCTTCGCTGA CACAATATGT ATAGGCTACC ATGCCAACAA CTCAACCGAC |
| 121 | ACTGTTGACA CAGTACTTGA GAAGAATGTG ACAGTGACAC ACTCTGTCAA CCTACTTGAG |
| 181 | GACAGTCACA ATGGAAAACT ATGTCTACTA AAAGGAATAG CCCCACTACA ATTGGGTAAT |
| 241 | TGCAGCGTTG CCGGATGGAT CTTAGGAAAC CCAGAATGCG AATTACTGAT TCCAAGGAA |
| 301 | TCATGGTCCT ACATTGTAGA ACACCAAAT CCTGAGAATG AACATGTTA CCCAGGGTAT |
| 361 | TTCGCCGACT ATGAGGAACT GAGCGAGCAA TTGAGTTCAG TATCTTCATT TGAGAGATTC |
| 421 | GAAATATTCC CCAAAGAAAG CTCATGGCCC AACCACACCG TAACCGGAGT ATCAGCATCA |
| 481 | TGCTCCCATA ATGGGAAAAG CAGTTTTTAC AGAAATTTGC TATGGCTGAC GGGGAAGAAT |
| 541 | GGTTTGTACC CAAACCTGAG CAAGTCCTAT GTAAACAACA AGAGAAAGA AGTCCTTGTA |
| 601 | CTATGGGGTG TTCATCACCC GCCTAACATA GGGAACCAAA GGGCACTCTA TCATACAGAA |
| 661 | AATGCTTATG TCTCTGTAGT GTCTTCACAT TATAGCAGAA GATTCACCCC AGAAATAGCC |
| 721 | AAAAGACCCA AAGTAAGAGA TCAGGAAGGA AGAATCAACT ACTACTGGAC TCTGCTGGAA |
| 781 | CCTGGGGATA CAATAATATT TGAGGCAAAT GGAAATCTAA TAGCGCCATG GTATGCTTTT |
| 841 | GCACTGAGTA GAGGCTTTGG ATCAGGAATC ATCACCTCAA ATGCACCAAT GGATGAATGT |
| 901 | GATGCGAAGT GTCAAACACC TCAGGGAGCT ATAAACAGCA GTCTTCCTTT CCAGAATGTA |
| 961 | CACCCAGTCA CAATAGGAGA GTGTCCAAAG TATGTCAGGA GTGCAAAATT AAGGATGGTT |
| 1021 | ACAGGACTAA GGAACATCCC ATCCATTCAA TCCAGAGGTT TGTTTGGAGC CATTGCCGGT |
| 1081 | TTCATTGAAG GGGGTGGAC TGGAATGGTA GATGGGTGGT ATGGTTATCA TCATCAGAAT |
| 1141 | GAGCAAGGAT CTGGCTATGC TGCAGATCAA AAAGTACAC AAAATGCCAT TAACGGGATT |
| 1201 | ACAAACAAGG TCAATTCTGT AATTGAGAAA ATGAACACTC AATTCACAGC TGTGGGCAAA |
| 1261 | GAGTTCAACA AATTGGAAAG AAGGATGGAA AACTTAAATA AAAAAGTTGA TGATGGGTTT |
| 1321 | CTAGACATTT GGACATATAA TGCAGAATTG TTGGTTCTAC TGGAAAATGA AAGGACTTTG |
| 1381 | GATTTCCATG ACTCCAATGT GAAGAATCTG TATGAGAAAG TAAAAAGCCA ATTAAAGAAT |
| 1441 | AATGCCAAAG AAATAGGAAA CGGGTGTTTT GAGTTCTATC ACAAGTGTAA CAATGAATGC |
| 1501 | ATGGAGAGTG TGAAAAATGG <u>TACC</u>TATGAC TATCCAAAAT ATTCCGAAGA ATCAAAGTTA |
| 1561 | AACAGGGAGA AAATTGATGG AGTGAAATTG GAATCAATGG GAGTATACta agagctcagg |
| 1621 | <u>cct</u>          SEQ ID NO:17 |

Fig. 6A

| | |
|---|---|
| 1 | <u>GGTACC</u>TATG ACTATCCAAA ATATTCCGAA GAATCAAAGT TAAACAGGGA GAAAATTGAT |
| 61 | GGAGTGAAAT TGGAATCAAT GGGA<u>GTATAC</u> CAGATTCTGG CGATCTACTC AACTGTCGCC |
| 121 | AGTTCCCTGG TTCTTTTGGT CTCCCTGGGG GCAATCAGCT TCTGGATGTG TTCCAATGGG |
| 181 | TCTTTGCAGT GTAGAATATG CATCtaagag ctcaggcct     SEQ ID NO:18 |

Fig. 6B

```
  1    GGTACCTATG ACTATCCAAA ATATTCCGAA GAATCAAAGT TAAACAGGGA GAAAATTGAT
 61    GGAGTGAAAT TGGAATCAAT GGGAGTATAC TCTGAGAAGG ATGAACTTta agagctcagg
121    cct         SEQ ID NO:19
```

Fig. 6C

```
  1    GGTACCTAT GACTATCCA AAATATTCC GAAGAATCA AGTTAAAC AGGGAGAAA
 61    ATTGATGGA GTGAAATTG GAATCAATG GGAGTATAC CACGATGAA CTTtaagagc
121    tcaggcct         SEQ ID NO:20
```

Fig. 6D

```
  1    GGTACCTATG ACTATCCAAA ATATTCCGAA GAATCAAAGT TAAACAGGGA GAAAATTGAT
 61    GGAGTGAAAT TGGAATCAAT GGGAGTATAC CTCAAACAAA TCGAAGACAA GATCGAAGAG
121    ATCCTCTCGA AAATCTACCA CATCGAAAAC GAGATTGCCA GGATCAAGAA GCTCATAGGC
181    GAGTCAGCAG CCtaagagct caggcct         SEQ ID NO:21
```

Fig. 6E

```
  1    GGTACCTATG ACTATCCAAA ATATTCCGAA GAATCAAAGT TAAACAGGGA GAAAATTGAT
 61    GGAGTGAAAT TGGAATCAAT GGGAGTATAC CTCAAACAAA TCGAAGACAA GATCGAAGAG
121    ATCCTCTCGA AAATCTACCA CATCGAAAAC GAGATTGCCA GGATCAAGAA GCTCATAGGC
181    GAGTCAGCAG CCTCTGAGAA GGATGAACTT taagagctca ggcct     SEQ ID NO:22
```

Fig. 6F

```
  1    GGTACCTATG ACTATCCAAA ATATTCCGAA GAATCAAAGT TAAACAGGGA GAAAATTGAT
 61    GGAGTGAAAT TGGAATCAAT GGGAGTATAC GGAGGCGCTG GCCCACCGCC AGTTCATCTA
121    CCGCCTCCGG TGCATCTGCC ACCTCCGGTT CACCTGCCAC CTCCGGTGCA TCTCCCACCG
181    CCAGTCCACC TGCCGCCTCC GGTCCACCTG CCACCGCCTG TCCATGTGCC GCCACCGGTT
241    CATCTGCCGC CTCCATCAGC AGCCtaagag ctcaggcct         SEQ ID NO:23
```

Fig. 6G

```
  1    GGTACCTATG ACTATCCAAA ATATTCCGAA GAATCAAAGT TAAACAGGGA GAAAATTGAT
 61    GGAGTGAAAT TGGAATCAAT GGGAGTATAC GGAGGCGCTG GCCCACCGCC AGTTCATCTA
121    CCGCCTCCGG TGCATCTGCC ACCTCCGGTT CACCTGCCAC CTCCGGTGCA TCTCCCACCG
181    CCAGTCCACC TGCCGCCTCC GGTCCACCTG CCACCGCCTG TCCATGTGCC GCCACCGGTT
241    CATCTGCCGC CTCCATCAGC AGCCTCTGAG AAGGATGAAC TTtaagagct caggcct
       SEQ ID NO:24
```

Fig. 6H

SOLUBLE RECOMBINANT INFLUENZA ANTIGENS

FIELD OF THE INVENTION

The present invention relates to the production of soluble recombinant influenza antigens. More specifically, the present invention is directed to the production of soluble recombinant influenza antigens that retain immunogenicity.

BACKGROUND OF THE INVENTION

Influenza is the leading cause of death in humans due to a respiratory virus. Common symptoms include fever, sore throat, shortness of breath, and muscle soreness, among others. During flu season, influenza viruses infect 10-20% of the population worldwide, leading to 250-500,000 deaths annually.

Influenza viruses are classified into types A, B, or C, based on the nucleoproteins and matrix protein antigens present. Influenza type A viruses may be further divided into subtypes according to the combination of hemagglutinin (HA) and neuraminidase (NA) surface glycoproteins presented. HA governs the ability of the virus to bind to and penetrate the host cell. NA removes terminal sialic acid residues from glycan chains on host cell and viral surface proteins, which prevents viral aggregation and facilitates virus mobility. Currently, 16 HA (H1-H16) and 9 NA (N1-N9) subtypes are recognized. Each type A influenza virus presents one type of HA and one type of NA glycoprotein. Generally, each subtype exhibits species specificity; for example, all HA and NA subtypes are known to infect birds, while only subtypes H1, H2, H3, H5, N1 and N2 have been shown to infect humans. Influenza viruses comprising H5 and H7 are considered the most highly pathogenic forms of influenza A viruses, and are most likely to cause future pandemics.

Influenza pandemics are usually caused by highly transmittable and virulent influenza viruses, and can lead to elevated levels of illness and death globally. The emergence of new influenza A subtypes resulted in 4 major pandemics in the 20$^{th}$ century. The Spanish flu, caused by an H1N1 virus, in 1918-1919 led to the deaths of over 50 million people worldwide between 1917 and 1920. The risk of the emergence of a new subtype, or of the transmission to humans of a subtype endemic in animals, is always present. Of particular concern is a highly virulent form of avian influenza (also called "bird flu"), outbreaks of which have been reported in several countries around the world. In many cases, this bird flu can result in mortality rates approaching 100% within 48 hours. The spread of the avian influenza virus (H5N1), first identified in Hong Kong in 1997, to other Asian countries and Europe has been postulated to be linked to the migratory patterns of wild birds.

There is increasing concern that the virus may become highly infectious for humans. The major problem for human health is the fact that influenza viruses are antigenically unstable, that is, they mutate rapidly. Should the avian influenza virus come into contact with human viruses, genetic reassortment of the avian virus could result in a highly pathogenic influenza virus that could causes severe disease or death in humans. Furthermore, such mutation could result in an influenza virus that is easily transmitted in humans.

The current method of combating influenza in humans is by annual vaccination. Each year, the World Health Organization selects 3 viral strains for inclusion in the annual influenza vaccine, which is produced in fertilized eggs. However, the number of vaccine doses produced each year is not sufficient to vaccinate the world's population. For example, Canada and the United-States obtain enough vaccines doses to immunize about one third of their population, while only 17% of the population of the European Union can be vaccinated. It is evident that current worldwide production of influenza vaccine would be insufficient in the face of a worldwide flu pandemic. Therefore, governments and private industry alike have turned their attention to the productions of effective influenza vaccines.

As previously mentioned, the current method of obtaining influenza virus vaccines is by production in fertilized eggs. The virus is cultured in fertilized eggs, followed by inactivation of the virus and purification of viral glycoproteins. While this method maintains the antigenic epitope and post-translational modifications, there are a number of drawbacks including the risk of contamination due to the use of whole virus and variable yields depending on virus strain. Sub-optimal levels of protection may result from genetic heterogeneity in the virus due to its introduction into eggs. Other disadvantages includes extensive planning for obtaining eggs, contamination risks due to chemicals used in purification, and long production times. Also, persons hypersensitive to egg proteins may not be eligible candidates for receiving the vaccine.

To avoid the use of eggs, influenza viruses have also been produced in mammalian cell culture, for example in MDCK or PERC.6 cells, or the like. Another approach is reverse genetics, in which viruses are produced by cell transformation with viral genes. These methods, however, also requires the use of whole virus as well as elaborate methods and specific culture environments.

The use of viral DNA as a vaccine has been explored. In this technology, protection is obtained by expression of viral antigens in human cells; the antigens are then recognized as foreign antigen, which leads to an specific antibody response. However, there exists the risk of oncogene activation from introduction of DNA into determinant portion of human cell genome—a significant drawback.

Vaccines comprising recombinant viral antigens expressed in viral DNA transformed insect or plant cells have also been prepared by Dow Agroscience (see, for example WO 2004/098530). While the risk associated with the use of live virus is avoided and the production process is shorter, protein conformation and post-translational modifications are affected. The scale-up and purification steps are also relatively complex as the antigens are associated with cellular membranes. In addition, the dose of baculovirus-recombinant HA required for effective immunization in animals is 10-fold higher than that of natural HA produced in fertilized eggs. In both cases, the levels of viral antigen expression are low.

In an effort to avoid the difficulties associated with purification of membrane proteins, Huang et al (2001, Vaccine, 19:2163-2171) replaced the transmembrane domain and the cytoplasmic tail of the measles HA with an ER retention signal. The resulting HA protein was produced in tobacco plant cells for the development of oral vaccine (edible vaccine). The HA expressed is not as strongly retained in the ER as it is with the transmembrane domain, thus simplifying the purification procedure. However, the natural trimeric form of HA cannot be formed in those conditions, which can affect the immunogenicity of the recombinant protein.

Saelens et al (1999, Eur. J. Biochm, 260:166-175) expressed an HA gene lacking the transmembrane domain in yeast (*Pichia pastoris*), leading to the secretion of monomeric HA. This form, however, was less immunogenic than the trimeric HA.

In order to protect the world population from influenza and to stave off future pandemics, vaccine manufacturers will need to develop effective, rapid methods producing vaccine doses. The current use of fertilized eggs to produce vaccines is insufficient and involves a lengthy process. Recombinant technologies offer promising approaches to the production of influenza antigens. However, the production of hemagglutinin has been limited to membrane-associated protein, which involves complex extraction processes with low yields, or to poorly-immunogenic soluble proteins.

SUMMARY OF THE INVENTION

The present invention relates to the production of soluble recombinant influenza antigens. More specifically, the present invention is directed to the production of soluble recombinant influenza antigens that retain trimeric assembly and immunogenicity.

It is an object of the present invention to provide soluble recombinant influenza antigens.

The present invention provides a recombinant hemagglutinin (rHA), comprising a hemagglutinin domain and an oligomerization domain. The rHA is produced as a soluble homotrimer. The protein may further comprise a signal peptide and/or an endoplasmic reticulum (ER) retention signal.

The present invention also provides a nucleotide sequence encoding the rHA as just described above.

The present invention further provides a nucleic acid sequence comprising a) a nucleotide sequence encoding a hemagglutinin domain; and b) a nucleotide sequence encoding an oligomerization domain. The nucleic acid encodes a soluble rHA that forms a homotrimer. The nucleic acid may further comprise a nucleotide sequence encoding a signal peptide and/or an endoplasmic reticulum (ER) retention signal.

The present invention also provides a vector comprising the nucleotide as described above.

The invention further provides a host cell expressing the rHA as described above, a host cell transformed with the nucleotide as just described above, or a host cell transformed with the vector as just described above.

It is also provided by the present invention, a method of producing a recombinant rHA protein. The method comprises providing a host cell with a vector comprising: a) a nucleotide sequence encoding a hemagglutinin domain, wherein the nucleic acid encodes a soluble rHA that forms a homotrimer; and b) a nucleotide sequence encoding an oligomerization domain, then expressing the rHA.

The present invention further provides a method of expressing a recombinant hemagglutinin (rHA) within a plant. In a first step, a vector comprising a nucleotide sequence encoding a hemagglutinin domain, wherein the nucleic acid encodes a soluble rHA that forms a homotrimer and a nucleotide sequence encoding an oligomerization domain, is introduced into a plant. In the step of introducing (step a), the nucleic acid may be introduced in the plant in a transient manner, or the nucleic acid is introduced in the plant so that it is stable.

The present invention also provides a method of producing a recombinant hemagglutinin (rHA) in a plant, comprising: a) introducing a nucleic acid sequence into the plant, or portion thereof, the nucleic acid sequence comprising a regulatory region operatively linked to a nucleotide sequence encoding a hemagglutinin domain and an oligomerization domain, wherein the nucleic acid encodes a soluble rHA that forms a homotrimer; and b) growing the transgenic plant, thereby producing the rHA. In the step of introducing (step a), the nucleic acid may be introduced in the plant in a transient manner, or the nucleic acid is introduced in the plant so that it is stable.

rHA is a very complex molecule to produce. Expression levels and yields of recombinant HA from current production systems are low; and consequently the production costs are high. This is mostly due to the complex trimeric structure of the protein, which must undergo a complex process for assembly during its synthesis. Furthermore, HA is a large protein that has a transmembrane domain, and is highly glycosylated. Producing a soluble form of HA would allow production at higher levels and decrease the complexity of the purification process. This would have an important impact on production costs. Replacing the transmembrane domain with soluble α-helices or other secondary structure suitable to stabilize HA structurally compatible with the coiled-coil core of the ectodomain of the HA protein is shown to yield stable, soluble HA trimers. Such recombinant proteins can be used to enrich current influenza vaccines, or in the preparation of new vaccines.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2 shows the amino acid sequence of the GCN4-pII peptide (SEQ ID NO:1).

FIG. 3 shows the amino acid and nucleotide sequences of PDI (SEQ ID NOs:6 and 7; (Genbank Accession Z11499), an alfalfa signal peptide. The PDI signal peptide is homologous to mouse ERp59. The BglII restriction site is indicated in bold.

FIG. 4 shows the amino acid sequence (SEQ ID NO:8) of HA from influenza strain A/New Caledonia/20/99 (H1N1) (Genbank Accession AY289929; Primary accession UniProt KB/TrEMBL: Q6WG00). The rHA signal peptide is shown in italics. The cleavage site of HA0 is indicated in bold and the fusion peptide is underlined. The transmembrane domain is shown in gray background.

FIG. 5 shows the amino acid sequences of various rHA constructs according to the present invention. The amino acid numbering has been adjusted according to the original amino acid numbering of HA. The PDI signal peptide is indicated in italics, the $HA_0$ cleavage site is shown in bold, the fusion peptide is underlined, and the stop codon is represented by *. FIG. 5A is the amino acid sequence (SEQ ID NO:9) of full length rHA comprising the PDI signal peptide and the transmembrane domain and cytoplasmic tail. The transmembrane domain is shown in gray background. FIG. 5B is the amino acid sequence (SEQ ID NO:10) of ER-retained rHA using the SEKDEL retention signal. The retention signal is shown in gray background. FIG. 5C is the amino acid sequence (SEQ ID NO:11) of ER-retained rHA using the HDEL retention signal. The retention signal is shown in gray background. FIG. 5D is the amino acid sequence (SEQ ID NO:12) of soluble rHA without the transmembrane domain. FIG. 5E is the amino acid sequence (SEQ ID NO:13) of soluble trimeric rHA using the GCN4-pII trimeric peptide. The GCN4-pII peptide is shown in gray background. FIG. 5F is the amino acid sequence (SEQ ID NO:14) of soluble trimeric rHA using the GCN4-pII trimeric peptide and retained in the ER. The GCN4-pII peptide is shown in gray background and the SKDEL retention signal is shown in italics. FIG. 5G is the amino acid sequence (SEQ ID NO:15) of soluble trimeric rHA using the PRD trimeric peptide. The PRD peptide is shown in gray background. FIG. 5H is the amino acid sequence (SEQ ID NO:16) of soluble trimeric rHA using the PRD trimeric peptide, and retained in the ER. The PRD peptide is shown in gray background and the retention signal is shown in italics.

FIG. 6 shows the nucleotide sequences of various fragments according to the present invention. The non-coding sequence is presented in small capitals and useful restriction sites are underlined. FIG. 6A shows the nucleotide sequence (SEQ ID NO:17) of the $HA_0$ gene fragment. FIG. 6B shows the nucleotide sequence (SEQ ID NO:18) of the transmembrane domain and the cytoplasmic tail gene fragment. FIG. 6C shows the nucleotide sequence (SEQ ID NO:19) of the ER-retained SEKDEL gene fragment. FIG. 6D shows the nucleotide sequence (SEQ ID NO:20) of the ER-retained HDEL gene fragment. FIG. 6E shows the nucleotide sequence (SEQ ID NO:21) of the GCN4-pII gene fragment. FIG. 6F shows the nucleotide sequence (SEQ ID NO:22) of the ER-retained GCN4-pII gene fragment. FIG. 6G shows the nucleotide sequence (SEQ ID NO:23) of the PRD gene fragment. FIG. 6H shows the nucleotide sequence (SEQ ID NO:24) of the ER-retained PRD gene fragment.

FIG. 9A shows results from *N. benthamiana*, while FIG. 9B shows results from *N. tabacum*. Lanes: 1) 5 µg of plant extracts for panels B, D and A, C respectively; 2) 1 ng of standard rHA spiked into 2 and 5 µg of plant extract for panels B, D and A, C, respectively; 3) Extract from biomass expressing construct #540; 4) Extract from biomass expressing construct #541; 5) Extract from biomass expressing construct #542; 6) Extract from biomass expressing construct #544; 7) Extract from biomass expressing construct #545; 8) Extract from biomass expressing construct #546; and 9) Extract from biomass expressing construct #547.

FIG. 10A shows results from *N. benthamiana*, while FIG. 10B shows results from *N. tabacum*. Lanes: 1) 5 µg of plant extract; 2) 1 ng of standard rHA spiked into 5 µg of plant extract; 3) Extract from biomass expressing construct #540; 4) Extract from biomass expressing construct #541; 5) Extract from biomass expressing construct #542; 6) Extract from biomass expressing construct #544; 7) Extract from biomass expressing construct #545; 8) Extract from biomass expressing construct #546; and 9) Extract from biomass expressing construct #547.

DESCRIPTION OF PREFERRED EMBODIMENT

The present invention relates to the production of soluble recombinant influenza antigens. More specifically, the present invention is directed to the production of soluble recombinant influenza antigens that retain immunogenicity.

The following description is of a preferred embodiment.

The present invention provides a recombinant hemagglutinin (rHA) comprising a hemagglutinin domain and an oligomerization domain. The recombinant protein is produced as a soluble homotrimer. The rHA may also comprise a signal peptide and/or an endoplasmic reticulum (ER) retention signal.

Influenza is caused by influenza viruses, which are classified into types A, B, or C. Type A and B viruses are most often associated with epidemics. Influenza type A viruses may be further divided into subtypes according to the combination of hemagglutinin (HA) and neuraminidase (NA) surface glycoproteins presented. Currently, 16 HA (H1-H16) and 9 NA (N1-N9) subtypes are recognized. Each type A influenza virus presents one type of HA and one type of NA glycoprotein.

By the term recombinant hemagglutinin, also referred to as "recombinant HA" and "rHA", it is meant a hemagglutinin protein that is produced by recombinant techniques, which are well known by a person of skill in the art. Hemagglutinin (HA) is an viral surface protein found on type A influenza viruses. To date, sixteen HA subtypes (H1-H16) have been identified. HA is responsible for binding of the virus to sialic acid residues of carbohydrate moieties on the surface of the infected host cell. Following endocytosis of the virus by the cell, the HA protein undergoes drastic conformational changes which initiate the fusion of viral and cellular membranes and virus entry into the cell.

Figure 1:
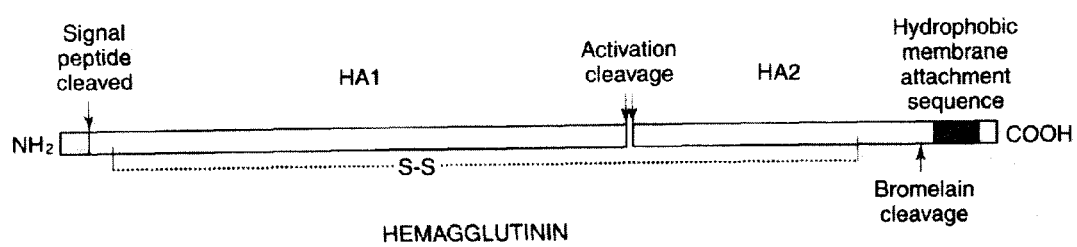
FIG. 1 shows a schematic of the domains of the naturally occurring hemagglutinin (HA) protein.
Figure 7:
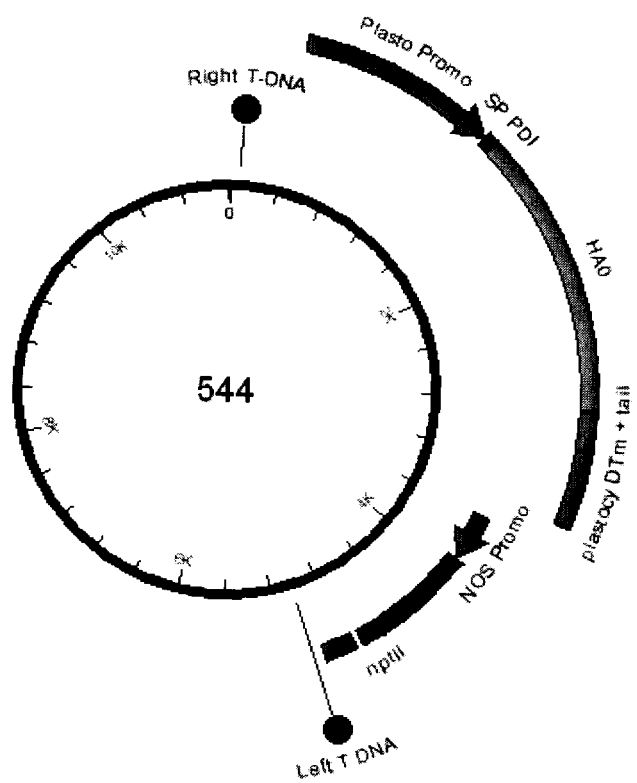
FIG. 7 is a schematic diagram of the rHA transfer DNA (t-DNA) in a pCAMBIA binary plasmid, in accordance with one embodiment of the present invention.
Figure 8:
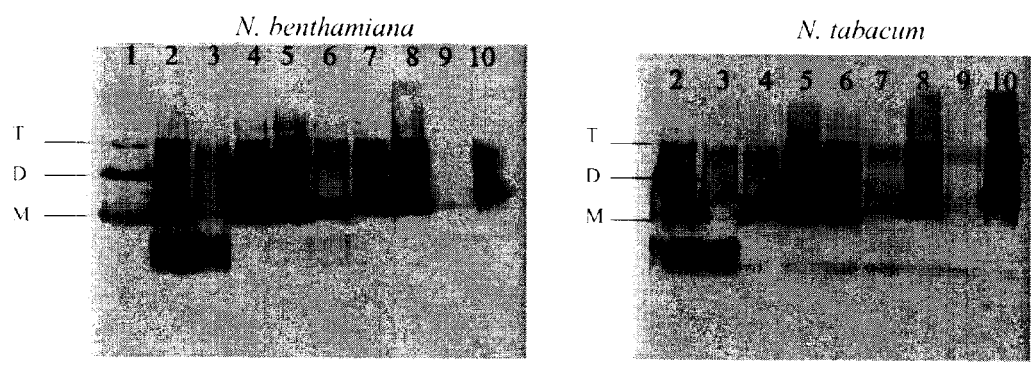
FIG. 8 is a Western blot showing the immunodetection of rHA expression in tobacco. Lanes: 1) Pure rHA standard (1 ng); 2) 1 ng of standard rHA spiked into 10 µg of plant extract; 3) 10 µg of plant extract; 4) 10 µg of protein extract from biomass expressing construct #540; 5) 10 µg of protein extract from biomass expressing construct #541; 6) 10 µg of protein extract from biomass expressing construct #542; 7) 10 µg of protein extract from biomass expressing construct #544; 8) 10 µg of protein extract from biomass expressing construct #545; 9) 10 µg of protein extract from biomass expressing construct #546; and 10) 10 µg of protein extract from biomass expressing construct #547.
Figure 9:
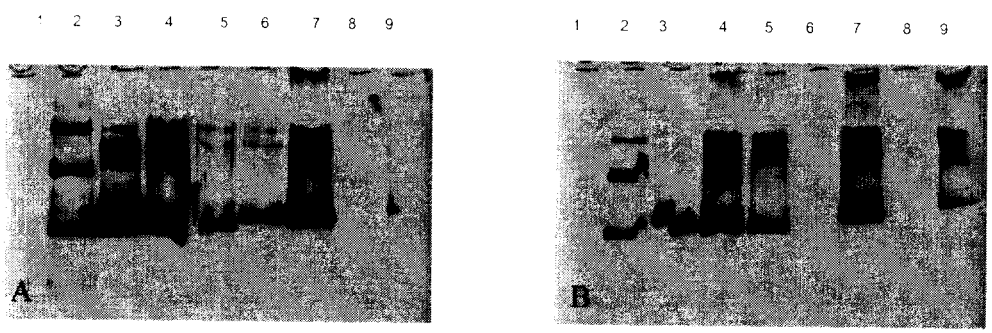
FIG. 9 is a Western blot showing the immunodetection of rHA expression in tobacco, with 5 µg pf extract.
Figure 10:
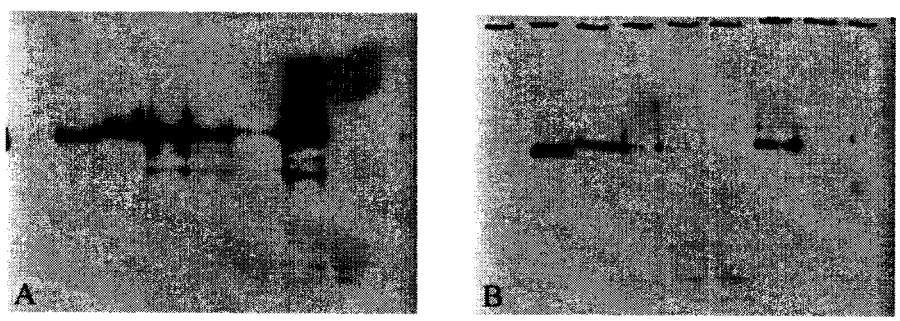
FIG. 10 is a Western blot showing the immunodetection of rHA expression in tobacco, with 5 µg pf extract, under reducing conditions.
Figure 11:
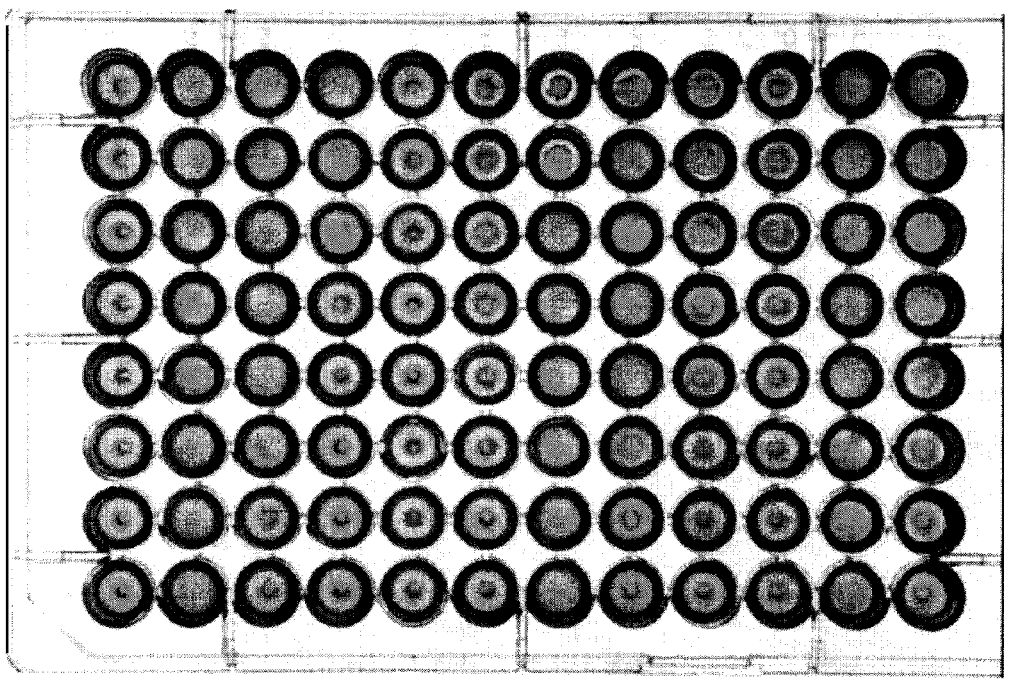
FIG. 11 shows a plate with results of a hemagglutination assay. Row 1: PBS (Negative control); Row 2: PBS+1000 ng HA (PSC); Row 3: PBS+100 ng HA (PSC); Row 4: PBS+10 ng of HA (PSC); Row 5: PBS+1 ng of HA (PSC); Row 6: Non-transformed plant extract; Row 7: Non-transformed plant extract+1000 ng HA (PSC); Row 8: Non-transformed plant extract+100 ng HA (PSC); Row 9: Non-transformed plant extract+10 ng HA (PSC); Row 10: Non-transformed plant extract+1 ng HA (PSC); Row 11: Plant extract expressing construct 540 (transmembranar rHA); and Row 12: Plant extract expressing construct 544 (soluble rHA fused to GCN4).

HA is a homotrimeric membrane type I glycoprotein, generally comprising a signal peptide, a $HA_0$ domain, a membrane-spanning anchor site at the C-terminus and a small cytoplasmic tail (FIG. 1). The term "homotrimer" or "homotrimeric" indicates that an oligomer is formed by three HA protein molecules. HA protein is synthesized as a 75 kDa monomeric precursor protein ($HA_0$), which assembles at the surface into an elongated trimeric protein. Before trimerization occurs, the precursor protein HA0 is cleaved at a conserved activation cleavage site (also referred to as fusion peptide) into 2 polypeptide chains, HA1 (328 amino acids) and HA2 (221 amino acids), linked by a disulfide bond. Although this step is central for virus infectivity, it is not essential for the trimerization of the protein. Insertion of HA within the endoplasmic reticulum (ER) membrane of the host cell, signal peptide cleavage and protein glycosylation are co-translational events. Correct refolding of HA requires glycosylation of the protein and formation of 6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains (Russell et al. 2004). It has also been established that HA undergoes major conformational changes during the infection process, which requires the precursor $HA_0$ to be cleaved into the 2 polypeptide chains HA1 and HA2.

The recombinant HA of the present invention may be of any subtype. For example, the HA may be of subtype H1, H2, H3, H4, H5, H6, H7, H8, H9, H10, H11, H12, H13, H14, H15, or H16. The rHA of the present invention may comprise an amino acid sequence based on the sequence any hemagglutinin known in the art. Furthermore, the rHA may be based on the sequence of a hemagglutinin that is isolated from emerging influenza viruses.

The rHA of the present invention may be a chimeric protein construct comprising a hemagglutinin domain and an oligomerization domain. The term "hemagglutinin domain" refers to an amino acid sequence comprising either the $HA_0$ domain, or the HA1 and HA2 domains. In other words, the rHA protein may be processed (i.e., comprises HA1 and HA2 domains), or may be unprocessed (i.e., comprises the $HA_0$ domain). The hemagglutinin domain does not include the signal peptide, transmembrane domain, or the cytoplasmic tail found in the naturally occurring protein. The "oligomerization domain", also referred to as "trimeric peptide", refers to a domain that promotes the oligomerization of the rHA protein. The oligomerization domain may be any amino acid sequence known in the art that promotes the formation of trimers. For example, the oligomerization domain may be a heterologous peptide, for example, leucine zippers or peptides adopting a coiled-coil structure. The oligomerization domain may be of a length and/or structure similar to the transmembrane domain it replaces, which is 26 amino acids in length. Alternatively, the oligomerization domain may be of length and/or structure similar to the transmembrane domain (26 amino acids) and the cytoplasmic tail (10 amino acids) that it replaces. For example, and without wishing to be limiting, the oligomerization domain may be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. In a specific, non-limiting example, the oligomerization domain is about 25-48 amino acids in length, or any amount therebetween. Non-limiting examples of suitable oligomerization domains include the GCN4-pII peptide (Harbury et al, 1993, Science, 262:1401-7), the proline-rich domain (PRD) of maize γ-zein, the bacteriophage T4 fibritin (Strelkov et al., 1996, Virology 219:190-194), or a trimerizing module identified in the fibronectin or collectin families.

In a specific, non-limiting example, the oligomerization domain may be the GCN4-pII peptide, a variant of the GCN4 yeast leucine zipper. This GCN4 mutant bears Ile residues at both a and d positions (pII), present at every 7 amino acids on the alpha-helix, leading to a high propencity for trimerization. The melting temperature (Tm) of the trimer is >100° C., conferring a high intrinsic stability to the oligomer (Harbour et al.). The amino acid sequence of GCN4-pII is shown in FIG. 2. GCN4-pII is well-suited for use as the oligomerization domain; the 29 amino acid sequence of GCN4-pII is placed at the C-terminal end of the HA domain sequence, essentially replacing the 26 amino acid transmembrane domain. If desired, additional amino acids may be placed at the C-terminal end of the rHA such that the recombinant structure does not terminate by an α-helix. For example, but without wishing to be limiting, Ser-Ala-Ala amino acid residues may be added at the C-terminal end of GCN4-pII.

In another example, the oligomerization domain may be the PRD of maize γ-zein, also referred to herein as "PRD".

Maize gamma-γ-Zein is known to store stacks in protein bodies once inside the ER. The synthetic PRD peptide adopts an amphipathic polyproline II conformation, which assembles itself as trimers (Kogan et al, 2002, Biophysical J., 83:1194-1204). In its natural form, the PRD comprises 8 repeats of the peptide PPPVHL (SEQ ID NO:2). The PRD peptide of maize gamma-γ-Zein is also placed at the C-terminus of the HA domain, replacing the transmembrane anchor. As the natural form of PRD is quite long, it is also within the scope of the present invention to provide the PRD in varying peptide lengths (4, 6 or 8 peptide repeats, i.e., 24, 36, or 48 amino acids in length). If desired, an amino acid linker may be placed between the HA domain and the PRD in order to permit the orientation of the PRD peptide chain towards a polyproline left helix. Any suitable peptide linker known in the art may be used. For example, and without wishing to be limiting in any manner, a tetrapeptide such as Gly-Gly-Ala-Gly (SEQ ID NO:3) may be used. Also if desired, additional amino acids may be placed at the C-terminal end of the rHA such that the recombinant structure does not terminate by an α-helix. For example, but without wishing to be limiting, Ser-Ala-Ala amino acid residues may be added at the C-terminal end of PRD.

In another non-limiting example, the oligomerisation domain may be the bacteriophage T4 fibritin (Strelkov et al., 1996, Virology 219:190-194). This domain comprises the last 29 amino acid residues at the C-terminal end of fibritin.

In yet another non limiting example, the oligomerization domain may be the trimerizing modules disclosed in WO 98/56906, incorporated herein by reference, which are trimerizing modules identified in the tetranectin family. The tetranectin trimerizing module also shows stability, in that its trimers were shown to exist at 60° C., or even 700° C. The trimerizing module may be covalently linked to the rHA, and is capable of forming a stable complex with two other trimerizing modules. Another example of oligomerization domain is the trimerizing peptides disclosed by WO 95/31540, incorporated herein by reference, which was identified in the collectin family. The peptides are about 25 to about 40 amino acids in length, and are derived from the neck region of proteins in the collectin family.

The rHA according to the present invention may further comprise a signal peptide. The signal peptide may be any suitable peptide known in the art, to direct the recombinant protein to the desired cell compartment or membrane. For example, and without wishing to be limiting, the signal peptide found in natural HA may be used, which directs HA the ER. In another non-limiting example, the signal peptide may be PDI, the alfalfa signal peptide. The amino acid and nucleotide sequences of PDI are shown in FIG. 3. Advantageously, the PDI signal peptide has a bg/II restriction site, which may be useful for cloning.

The rHA as described above may also further comprise an endoplasmic reticulum (ER) retention signal. Any suitable ER retention signal known by a person of skill in the art may be used. For example, but without wishing to be limiting in any manner, the Ser-Glu-Lys-Asp-Glu-Leu (SEKDEL; SEQ ID NO:4) or the His-Asp-Glu-Leu (HDEL; SEQ ID NO:5) ER retention signals may be used. The chosen ER retention signal may be at the C-terminal end of the rHA protein sequence. Advantageously, ER-retention of a recombinant protein in plants has been shown in several cases to improve the expression level by 2- to 10-fold (Schillberg et al, 2003, Cell Mol. Life Sci. 60:443-445). Without wishing to be bound by theory, the ER retention signals may allow back and forth movement of proteins between the ER and the Golgi complex, which allows trimerization to occur.

The term "soluble" indicates that the rHA is produced in the host cell in a soluble form. As described above, the conversion of recombinant HA to a soluble form arises from the replacement of the transmembrane hydrophobic domain by a soluble α-helices that are structurally compatible with the HA domain. Expressing the rHA in a soluble form may increase yields (higher expression levels) and decrease the complexity of purification, therefore lowering the production costs.

The present invention also provides a nucleic acid encoding the rHA as described above. The nucleic acid is a chimeric construct comprising a nucleotide sequence encoding a hemagglutinin domain ($HA_0$) and a nucleotide sequence encoding an oligomerization domain. The nucleic acid encoding the rHA may also comprise a nucleotide sequence encoding a signal peptide and/or a nucleotide sequence encoding an ER retention signal.

The present invention is further directed to a chimeric gene construct comprising a nucleic acid encoding rHA, as described above, operatively linked to a regulatory element. By "regulatory element" or "regulatory region", it is meant a portion of nucleic acid typically, but not always, upstream of a gene, and may be comprised of either DNA or RNA, or both DNA and RNA. Regulatory elements may include those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. By a nucleotide sequence exhibiting regulatory element activity it is meant that the nucleotide sequence when operatively linked with a coding sequence of interest functions as a promoter, a core promoter, a constitutive regulatory element, a negative element or silencer (i.e. elements that decrease promoter activity), or a transcriptional or translational enhancer.

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

Regulatory elements as used herein, also includes elements that are active following transcription initiation or transcription, for example, regulatory elements that modulate gene expression such as translational and transcriptional enhancers, translational and transcriptional repressors, and mRNA stability or instability determinants. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as listed above) that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, may be operatively associated (operatively linked) with heterologous regulatory elements or promoters in order to modulate the activity of the heterologous regulatory element. Such modulation includes enhancing or repressing transcriptional activity of the heterologous regulatory element, modulating post-transcriptional events, or both enhancing/repressing transcriptional activity of the heterologous regulatory element and modulating post-transcriptional events. For example, one or more regulatory elements, or fragments thereof, may be operatively associated with constitutive, inducible, tissue specific promoters or fragment thereof, or fragments of regulatory elements, for example, but not limited to TATA or GC sequences may be operatively associated with the regulatory elements of the present invention, to modulate the activity of such promoters within plant, insect, fungi, bacterial, yeast, or animal cells There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within a plant as well.

By "promoter" it is meant the nucleotide sequences at the 5' end of a coding region, or fragment thereof that contain all the signals essential for the initiation of transcription and for the regulation of the rate of transcription. There are generally two types of promoters, inducible and constitutive promoters. If tissue specific expression of the gene is desired, for example seed, or leaf specific expression, then promoters specific to these tissues may also be employed.

An inducible promoter is a promoter that is capable of directly or indirectly activating transcription of one or more DNA sequences or genes in response to an inducer. In the absence of an inducer the DNA sequences or genes will not be transcribed. Typically the protein factor that binds specifically to an inducible promoter to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods. Examples of inducible promoters include, but are not limited to plant promoters such as: the alfalfa plastocyanine promoter (see, for example WO01/025455), which is light-regulated; the alfalfa nitrite reductase promoter (NiR; see for example W001/025454, which can be induced by fertilization with nitrates (3); and the alfalfa dehydrine promoter (U.S. Application Ser. No. 60/757,486), which is induced by environmental stresses such as cold.

A constitutive promoter directs the expression of a gene throughout the various parts of a plant and continuously throughout plant development. Any suitable constitutive promoter may be used to drive the expression of rHA within a transformed cell, or all organs or tissues, or both, of a host organism. Examples of known constitutive promoters include those associated with the CaMV 35S transcript. (Odell et al., 1985, *Nature*, 313: 810-812), the rice actin 1 (Zhang et al, 1991, *Plant Cell*, 3: 1155-1165) and triosephosphate isomerase 1 (Xu et al, 1994, *Plant Physiol.* 106: 459-467) genes, the maize ubiquitin 1 gene (Cornejo et al, 1993, *Plant Mol. Biol.* 29: 637-646), the *Arabidopsis* ubiquitin 1 and 6 genes (Holtorf et al, 1995, *Plant Mol. Biol.* 29: 637-646), and the tobacco translational initiation factor 4A gene (Mandel et al, 1995 *Plant Mol. Biol.* 29: 995-1004).

The term "constitutive" as used herein does not necessarily indicate that a gene is expressed at the same level in all cell types, but that the gene is expressed in a wide range of cell types, although some variation in abundance is often observed.

The chimeric gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3Y end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes and the small subunit of the ribulose-1, 5-bisphosphate carboxylase (ssRUBISCO) gene. The 3' untranslated region from the structural gene of the present construct can therefore be used to construct chimeric genes for expression in plants. Other examples of suitable 3' regions are terminators, which may include, but are not limited to the noncoding 3' region of the sequence of the plastocyanine or the nitrite reductase or the dehydrine alfalfa genes.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

Also considered part of this invention are plants, portion or tissues of plants, plant cells, trees, portion of trees, tree cells, yeast, bacteria, fungi, insect and animal cells containing the chimeric gene construct comprising a nucleic acid encoding rHA, in accordance with the present invention. However, it is to be understood that the regulatory elements of the present invention may also be combined with coding region of interest for expression within a range of host organisms that are amenable to transformation. Such host organisms include, but are not limited to:

plants, both monocots and dicots, for example, corn, cereal plants, wheat, barley, oat, tobacco, *Brassica*, soybean, bean, pea, alfalfa, potato, tomato, ginseng, *Arabidopsis*; a portion or tissue of these plants for example, leaves, roots, stems, meristem, floral structure, cells of these plants and yeast, fungi, insects, animal and bacteria cells.

Methods for the transformation and regeneration of these organisms are established in the art and known to one of skill in the art and the method of obtaining transformed and regenerated plants is not critical to this invention.

By "transformation" it is meant the interspecific transfer of genetic information (nucleotide sequence) that is manifested genotypically, phenotypically, or both. The interspecific transfer of genetic information from a chimeric construct to a host may be heritable and the transfer of genetic information considered stable, or the transfer may be transient and the transfer of genetic information is not inheritable.

Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J Virol Meth, 105:343-348, 2002,), U.S. Pat. Nos. 4,945,050; 5,036,006; and 5,100,792, U.S. patent application Ser. Nos. 08/438,666, filed May 10, 1995, and 07/951,715, filed Sep. 25, 1992, (all of which are hereby incorporated by reference).

As described below, transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al., 1997, which is incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or synringe infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacteria* infect and transfer t-DNA copies into the cells. The t-DNA is episomally transcribed and the mRNA translated, leading to the production of the protein of interest in infected cells, however, the passage oft-DNA inside the nucleus is transient.

To aid in identification of transformed plant cells, the constructs of the present invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

When specific sequences are referred to in the present invention, it is understood that these sequences include within their scope sequences that are "substantially homologous" to the specific sequences, or sequences or a compliment of the sequences hybridise to one or more than one nucleotide sequence as defined herein under stringent hybridisation conditions. Sequences are "substantially homologous" when at least about 70%, or more preferably 75% of the nucleotides match over a defined length of the nucleotide sequence providing that such homologous sequences exhibit one or more than one regulatory element activity as disclosed herein.

Such a sequence similarity may be determined using a nucleotide sequence comparison program, such as that provided within DNASIS (using, for example but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (GAP, BESTFIT, FASTA, and BLAST, available through the NIH.), or by manual alignment and visual inspection (see, e.g., Current Protocols in Molecular Biology, Ausubel et al., eds. 1995 supplement), or using Southern or Northern hybridization under stringent conditions (see Maniatis et al., in Molecular Cloning (A Laboratory Manual), Cold Spring Harbor Laboratory, 1982). Preferably, sequences that are substantially homologous exhibit at least about 80% and most preferably at least about 90% sequence similarity over a defined length of the molecule.

An example of one such stringent hybridization conditions may be overnight (from about 16-20 hours) hybridization in 4×SSC at 65° C., followed by washing in 0.1×SSC at 65° C. for an hour, or 2 washes in 0.1×SSC at 65° C. each for 20 or 30 minutes. Alternatively an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each for unique sequence regions.

The rHA of the present invention can be used in conjunction with existing influenza vaccines, to supplement the vaccines, render them more efficacious, and to reduce the administration dosages necessary. As would be known to a person of skill in the art, the vaccine may be directed against one or more than one influenza virus. Examples of suitable vaccines include, but are not limited to those commercially available from Sanofi-Pasteur, ID Biomedical, Merial, Sinovac, Chiron, Roche, MedImmune, GlaxoSmithKline, and the like.

The invention will now be described in detail by way of reference only to the following non-limiting examples.

Example 1 rHA Strategy

The HA chosen to exemplify the present invention was obtained from influenza strain A/New Caledonia/20/99 (H1N1). The A/New Caledonia/20/99 HA has been well characterized and immunodetection tools are commercially available. As the three-dimensional structures of all HAs are well conserved, the present expression strategy can directly apply to any other HA.

The expression of rHA was directed to the ER and the secretory pathway using the signal peptide of the alfalfa PDI (SEQ ID NO:3). This signal peptide was fused directly to the N-terminal primary sequence of mature rHA (FIG. 4; SEQ ID NO:8). The theoretical cleavage of the signal peptide from mature rHA with the PDI signal peptide was verified using the SignalP server 3.0.

rHA can be retained in the ER using the SEKDEL (SEQ ID NO:4) or the HDEL (SEQ ID NO:5) retention signals, both fused to the C-terminal end of rHA protein sequence.

When the GCN4-pII peptide was used as the oligomerization domain, it was fused directly to C-terminal of the last Tyr residue of $HA_0$. The Met residue at position 1 of GCN4-pII was changed to a Leu because Leu is more inert than Met and it has similar packing volume compared to the original Met. Amino acids Ser-Ala-Ala were added at the C-terminus of GCN4-pII.

When the PRD of maize gamma-γ-Zein was used, a peptide with 8 repetitions of the PPPVHL (SEQ ID NO:2) was fused to HA, to replace the transmembrane domain of HA. The 4 first proline residues were also included in the fusion. The C-terminal cysteine was excluded. To accommodate the fusion of a polyproline helix to the C-terminus of HA, the peptide Gly-Gly-Ala-Gly (SEQ ID NO:3) was added the N-terminal of PRD. The Ser-Ala-Ala peptide was added to the C-terminus of PRD.

In total, 8 different rHA gene constructs were prepared to test their expression in planta:

1. The full length rHA, including the transmembrane domain, with the PDI signal peptide (SEQ ID NO:9);
2. The transmembrane domain and cytoplasmic tail were removed from the rHA of item 1 and replaced by the retention signal SEKDEL (SEQ ID NO:10);
3. The transmembrane domain and cytoplasmic tail were removed from the rHA of item 1 and replaced by the retention signal HDEL (SEQ ID NO:11);
4. The transmembrane domain and cytoplasmic tail were removed from the rHA of item 1 (SEQ ID NO:12);
5. The transmembrane domain and cytoplasmic tails were removed from the rHA of item 1 and replaced by the GCN4-pII (SEQ ID NO:13);
6. The transmembrane domain and cytoplasmic tails were removed from the rHA of item 1 and replaced by the GCN4-pII, with the SEKDEL retention signal at the C-terminus (SEQ ID NO:14);
7. The transmembrane domain and cytoplasmic tails were removed from the rHA of item 1 and replaced by the PRD domain (SEQ ID NO:15); and 8. The transmembrane domain and cytoplasmic tails were removed from the rHA of item 1 and replaced by the PRD domain, with the SEKDEL retention signal at the C-terminus (SEQ ID NO:16).

Example 2

Gene Synthesis

The eight different gene constructs described in Example 1 were synthesized. The wild-type nucleotide sequence of HA from influenza strain A/New Caledonia/20/99 was only modified to insert or remove restriction sites to facilitate the cloning steps. These minor modifications in the gene sequence did not change the resulting amino acid sequence of the protein. The $HA_0$ gene was synthesized with an ApaI restriction site at the 5'-end, in phase with the ATG of the PDI signal peptide. The 7 other genes bear a KpnI restriction site at their 5'-end. Every gene ends at the 3' end with a stop codon (TAA), followed by a SacI and a StuI restriction sites. According to the designed cloning strategy, the following restriction sites were design to be unique in the final plasmid: ApaI, BstZ17 I, Sac I, Kpn I, Bgl II, and Stu I. The different gene fragments were synthesized at the Plant Biotechnology Institute and were delivered cloned into pUC18. Selected nucleotide sequence information is given in FIG. 6 (SEQ ID NOs: 17-24).

Example 3

Genetic Assembly of Vectors Expressing rHA Fusions

The various DNA constructs were assembled using known recombinant DNA techniques (Sambrook et al (1989) Molecular cloning: A laboratory Manual, Sec Ed. Cold Spring Harbor Laboratory press, Cold Spring Harbor, N.Y.). The *E. coli* DH5α strain was used has a host for amplification of the binary vectors, unless otherwise specified. The $HA_0$ gene fragment was ligated directly into the plastocynine cassette (already containing the pdi signal peptide) using the bglII and SacI restriction sites, or was co-ligated with the 7 other C-terminus ends using the KpnI, bglII and Sad restriction sites. In each case, the gene was inserted into a plastocyanine expression cassette contained on transfer DNA (t-DNA) of a binary vectors. t-DNA is the part of the binary vector that is integrated in the genome (from the right to the left border) of the host plant cell upon transformation. The binary vectors used in this example were derived from the commercial plasmid pCAMBIA 2300 (Cambia, Canberra, Au) and contained, from the right to left borders sequences of the t-DNA, the following elements:

various proprietary expression cassettes (promoter and terminator), available from Medicago, where the rHA genes are inserted;

a multiple cloning site to facilitate the cloning; and the gene coding for neomycin phosphotansferase II (nptII), a selectable marker that confers resistance to kanamycin, under the control of a nopaline synthase (NOS) promoter and a cauliflower 35S mosaic virus (35S) terminator.

Each clone was submitted to DNA sequencing to verify the nucleotide sequence of the clones. Nucleotide variations were tolerated in the sequence of the rHA gene, provided the resulting amino acid sequence still encoded the exact same protein sequence (SEQ ID NOs:9-16). The 8 different DNA constructs are listed in Table 1, and an example of the resulting rHA t-DNA is shown schematically in FIG. 7.

TABLE 1

DNA constructs for rHA

| No. | Expression strategy | Sub-cellular targeting | ER retention signal | SEQ ID NO: |
|---|---|---|---|---|
| 540 | Complete transmembrane secreted | Apoplast | | 9 |
| 541 | ER-retained | ER | SEKDEL | 10 |
| 542 | ER-retained | ER | HDEL | 11 |
| 543 | Soluble, secreted | Apoplast | | 12 |
| 544 | Soluble trimeric GCN4 | Apoplast | | 13 |
| 545 | Soluble trimeric GCN4 | ER | SEKDEL | 14 |
| 546 | Soluble trimeric PRD | Apoplast | | 15 |
| 547 | Soluble trimeric PRD | ER | SEKDEL | 16 |

DNA isolated from *E. coli* proper clones was finally inserted into *Agrobacterium tumefaciens* Agl1 or other strains. The list of the *Agrobacterium* clones containing the various t-DNAs used in the present invention appears at Table 1. In preparation for plant transient expression experiments, plasmidic DNA was isolated from *Agrobacterium* clones and submitted restriction digest mapping to ensure integrity of the DNA Example 3

Transient Expression of rHA in Tobacco

*Agrobacterium* growth. The *Agrobacterium* clones containing a binary vector bearing rHA DNA constructs (Table 1) were grown for 24 hours at 28° C. in 2 mL of YEB or LB medium containing 25 and 50 μg/mL of each carbenicilin and kanamycin, respectively. 10 μL of these cultures were used as starting inoculums to generate cultures of 25 mL of YEB induction medium (YEB medium, 10 mM 2 (N morpholino) ethanesulfonic acid (MES), pH adjusted to 5.6, 25 mg/L carbenicillin, 50 mg/L kanamycin, 20 μM acetosyringone). The latter were grown in rotary shaker (220 rpm) incubator at 28° C. for 18 hours or until an optical density at 600 nm (OD600) of 0.8 to 1 was reached.

Growth of non-transgenic tobacco. *Nicotiana benthamiana* and *Nicotiana tabacum* plants were grown from seeds in a peat-based substrate (AgroMix) in a greenhouse. Seedlings were initially raised in a nursery and later transplanted to pots. Plants were irrigated twice a day and receive 180 ppm of nitrogen at each application. Greenhouse condition were kept at 25° C. during the day and 21° C. during the night, under a long day photoperiod regime (16 h light/8 h dark cycles), with artificial lightning of 20 watt m-2 at plant level.

Transient expression of rHA tobacco. The *Agrobacterium* culture prepared as described earlier was centrifuged 8 min at 10 000 g, resuspended in the same volume of inoculation medium (10 mM MgCl2, 10 mM MES, adjusted to pH 5.6, and supplemented with 100 μM acetosyringone) and kept at room temperature (RT, 23° C.) for 1 h prior to inoculation. Alternatively, the suspension can be kept at 4° C. for 24 hours prior to inoculation. Transient transformation of *N. benthamiana* and *N. tabacum* were essentially performed as described in Liu and Lomonossoff (2002, Journal of Virological Methods, 105:343-348), with the following modifications. For the expression of rHA, a mixture of two *Agrobacteria* strains was inoculated. The first strain contained one of the clones described at Table 1 and the second strain contained the HcPro suppressor of silencing from the Potato Virus Y under the control of the 35S promoter. After inoculation, the plants were incubated in a greenhouse. Temperature was kept at a minimum 23° C. during the day and 21° C. during the night. Plants were irrigated twice a day and received 180 ppm of nitrogen at each application. Harvest of biomass was undertaken after 4-8 days.

Example 5

Demonstration of Expression of rHA in Tobacco Leaves

Preparation of a soluble protein extracts from inoculated leaves. Leaves were analyzed directly after harvesting or after freezing the biomass at −80° C. A vegetable biomass of Agro-inoculated leaves of ~0.1 g was weighted and used for analysis of rHA transient expression.

One of two extraction methods was used to generate a total protein extract: by grounding the vegetable tissue with a mortar and a pestle, or by pulverizing it in a MixerMill300 (MM300) from Retsch. 0.1 g of plant biomass was transferred into a clean and pre-cooled mortar. 0.3 mL of cold extraction buffer (Tris 50 mM pH 7.4 containing NaCl 150 mM, 0.1% Triton X-100, and 5% glycerol) was added as well as PMSF and chymostatin to final concentrations of 1 mM and 10 μM, respectively. Leaves were ground with a pestle until a homogeneous preparation was obtained. The plant extract was then transferred into a 1.5 mL microtube and centrifuged at 20,000 g for 20 min at 4° C. Alternatively, 0.1 g of plant tissue with 0.3 mL of extraction buffer was introduced into non-sterile 1.5 microtube. A tungsten bead was added to each tube. The box was submitted to 3 min cycle of agitation at 30 Hz. The cycle was repeated 2 times. The plant extracts were then centrifuged as described above.

Following centrifugation, the supernatant was transferred into a clean microtube and maintained on ice. Finally, the total protein content of individual protein extracts was measured by the Bradford method using BSA as the reference protein.

Immunodetection of rHA transiently expressed in tobacco leaf material. The Agro-inoculated tobacco leaf protein extracts was prepared as described above. The following 3 controls were also prepared: 1) 1 ng of pure rHA (recombinant rHA produced by CHO cells, Protein Sciences Corporation, catalog #3006) to which 1 μg of BSA (Pierce) was added, 2) 2-10 μg of tobacco protein extract obtained from a biomass agro-inoculated with agrobacteria transformed with an empty pCAMBIA plasmid, and 3) 1 ng of pure rHA spiked to 2-10 μg of the protein extract of sample #2.

Typically, 2-10 μg of protein extract from each biomass (transformed with one of the 8 different DNA constructs, see Table 1) was loaded on SDS-PAGE for Western blot analysis. Samples were boiled for 5 min at 100° C. prior to loading on denaturing SDS-PAGE (concentration 6% acrylamide; separation 10% acrylamide, Tris-glycine buffer) as essentially described by Thomas (1975, Proc. Nat. Acad. Sci. USA, 72:2626-2630). Electrophoresis was performed at 110 volts for 90 min using Mini Protean III apparatus (BioRad). Separated proteins were then blotted onto a PVDF membrane in a Tris 25 mM, Glyine 192 mM, Methanol 10% (v/v) pH 8.3 buffer at 100 V for 30 min or 60 min when using a Criterion blotter or a Mini-trans blot Unit (BioRad), respectively.

Immunodetection of rHA was achieved with the following antibodies. A mouse monoclonal antibody to influenza A virus (Fitzgerald Industries International Inc. Catalog #10-150) was used as the primary antibody at 1/1,000. The secondary antibody was a peroxidase conjugated goat anti-mouse IgG (H+L) (Jackson ImmunoResearch #111-035-146) used at 1/10,000. The peroxydase activity was detected using Immobilon Western Chemiluminescent HRP substrate (Milipore, catalog #WBRL50100) or BM chemiluminescent blotting substrate (POD) (Roche, catalog #11500 694 001).

The immunodetection method was optimized to obtain a specific signal against each rHA, without cross-reactivity with endogenous plant proteins. The limit of detection was low; which allowed detection of the proteins expressed at levels as low as >0.004% (1 ng into 25 μg of extract) of total soluble proteins (TSP).

As shown in FIG. 8, rHA was expressed in every condition tested and in both tobacco species. The use of non-reducing conditions allowed detection of different oligomeric forms of hemagglutinin: monomers, dimers and trimers. With decreasing quantities of protein loaded on the gel, as examplified at FIG. 9, the oligormeric forms of rHA are resolved. The latter are the same for every construct tested and in both tobacco species: immunodetection signals are observed at the level of the trimer and of the monomer. A third immunoreactive band is also observed, which migrates between the expected molecular weight of the dimer and that of the trimer.

The replacement of the transmembrane domain by the different trimeric coil-coiled peptides allowed expression of rHA with expression levels equal to or higher than the transmembrane form of rHA. This is especially true for the fusion with GCN4-pII. The fusion of rHA with the PRD allows expression at lower levels compared to the GCN4-pII fusion. The expression levels of the GCN4-pII-rHA fusion is of, at least, 0.01% TSP (>1 ng of rHA in 10 μg of TSP). Accumulation of rHA fusions appears higher in *N. benthamiana* compared to *N. tabacum*. Finally, retention of rHA to the ER, for every construct tested, increases significantly the expression levels of rHA. This tendency has been observed for many other proteins. The ER subcellular space is generally recognized for its low proteolytic activity compared to other compartments such as the apoplast, resulting in higher accumulation of recombinant proteins.

The same protein extracts were analysed under reducing conditions and immunodetected as described earlier to investigate whether the $HA_0$ chain is proteolysed into the two-chain form of rHA, i.e., HA1 and HA2. The expected molecular weights of the latter are 47 and 28 kDa, respectively. It is shown at FIG. 10 that the $HA_0$ is not readily converted to a two-chain form. It is worth noticing that proteolysis or clipping of rHA appears to be greater in the *N. tabacum* extracts.

Example 6

Demonstration of Trimeric Assembly of rHA

Hemagglutination test. The hemagglutination assay was performed essentially as described by Nayak et al. (2004, J. Virol Methods, 122:9-15), with the following modifications. Extracts were prepared by homogenization of tissue in 50 mM Tris pH 7.4, 150 mM NaCl, 0.1% Triton X-100, and containing PMSV 1 MM and Chymostatin 10 μM as protease inhibitors. Soluble fractions were diluted to 0.2 mg/mL in PBS. Serial double dilutions of the tamples (100 μL) were made in round-bottomed 96-well microplate containing 100 μL of PBS. 100 μL of red blood chicken cells ($2\times10^7$ rbc/mL) (Innovative Research, South Field, Mich., USA) were added to each well. The plate was then incudated for 60-120 min at room temperature. Assay includes the following positive controls: rHA from PSC, ranged from 1 μg to 7.8 pg, diluted in PBS or spiked in non-transformed extract. A negative control using non-transformed extract was also run.

The hemagglutination assay was used to demonstrate the trimeric assembly of rHA fused to the coiled-coli peptides: That test, although very simple, is used on a routine basis to quantify the influenza titer. The principle of the assay is: free red blood cell roll will roll at the bottom an ELISA well, forming a cellular pile of red blood cells that can be easily detected. If hemagglutination occurs, the blood cell will form a matrix so the the blood cell can not roll at the bottom the ELISA well and no point can be seen. FIG. 11 shows that hemagglutination of chicken red blood cell can be performed directly on rHA expressed in a plant extract. More over the hemagglutination can occur with a plant extract expressing the rHA fused to GCN4-pII. Since the rHA monomer is unable to undergo red blood cell hemagglutination, that result ultimately demonstrates that the chimeric rHA assemble itself as a trimer in the plant.

Table 2 summarizes the sequences listed in the present application.

TABLE 2

Sequence description for sequence identifiers.

| SEQ ID NO: | Sequence description |
|---|---|
| 1 | Amino acid sequence of the GCN4-pII peptide |
| 2 | peptide repeat of the PRD peptide of maize gamma-γ-Zein |
| 3 | tetrapeptide linker |
| 4 | SEKDEL ER retention signal |
| 5 | HDEL ER retention signal |
| 6 | amino acid sequence of the alfalfa PDI signal peptide |
| 7 | nucleotide sequence of the alfalfa PDI signal peptide |
| 8 | Amino acid sequence of mature HA |
| 9 | full length rHA, including the transmembrane domain, with the HA signal peptide replaced by the PDI signal peptide |
| 10 | SEQ ID NO: 9, with the transmembrane domain and cytoplasmic tail replaced by the retention signal SEKDEL |
| 11 | SEQ ID NO: 9, with the transmembrane domain and cytoplasmic tail replaced by the retention signal HDEL; |
| 12 | SEQ ID NO: 9, without the transmembrane domain and cytoplasmic tail |
| 13 | SEQ ID NO: 9, with the transmembrane domain and cytoplasmic tail replaced by the GCN4-pII peptide |
| 14 | SEQ ID NO: 13, with the SEKDEL retention signal at the C-terminus |
| 15 | SEQ ID NO: 9, with the transmembrane domain and cytoplasmic tail replaced by the PRD domain |
| 16 | SEQ ID NO: 15, with the SEKDEL retention signal at the C-terminus |
| 17 | the nucleotide sequence of the $HA_0$ gene fragment |
| 18 | the nucleotide sequence of the transmembrane domain and the cytoplasmic tail gene fragment |
| 19 | the nucleotide sequence of the ER-retained SEKDEL gene fragment. |
| 20 | the nucleotide sequence of the ER-retained HDEL gene fragment |
| 21 | the nucleotide sequence of the GCN4-pII gene fragment |
| 22 | the nucleotide sequence of the ER-retained GCN4-pII gene fragment |
| 23 | the nucleotide sequence of the PRD gene fragment |
| 24 | the nucleotide sequence of the ER-retained PRD gene fragment |

The present invention has been described with regard to one or more embodiments. However, it will be apparent to persons skilled in the art that a number of variations and modifications can be made without departing from the scope of the invention as defined in the claims.

The contents of all references and patents cited throughout this application are hereby incorporated by reference in their entirety.

The embodiments of the invention in which an exclusive property or privilege is claimed are defined as follows:

1. A recombinant hemagglutinin (rHA), comprising:
   a) a hemagglutinin domain selected from the group consisting of hemagglutinin subtypes H1, H2, H3, H4, H5, H6, H7, H8, H9, H10, H11, H12, H13, H14, H15, and H16; b) an oligomerization domain selected from the group consisting of a GCN4-pII peptide, a proline rich domain (PRD) of maize γ-zein, and a bacteriophage T4 fibritin;
   wherein amino acid residues are added to the C-terminal end of the oligomerization domain such that the oligomerization domain from GCN4-pII or bacteriophage T4 fibritin does not terminate in an α-helix and the oligomerization domain from the PRD of maize γ-zein does not terminate in an amphipathic polyproline II helix;
   c) a signal peptide; and
   d) an endoplasmic reticulum (ER) retention signal;
   wherein the rHA is produced as a chimeric soluble homotrimer.

2. A nucleotide sequence encoding the rHA of claim 1.

3. A nucleic acid comprising:
   a) a nucleotide sequence encoding a hemagglutinin domain selected from the group consisting of hemagglutinin subtypes H1, H2, H3, H4, H5, H6, H7, H8, H9, H10, H11, H12, H13, H14, H15, and H16;
   b) a nucleotide sequence encoding an oligomerization domain selected from the group consisting of a GCN4-pII peptide, a proline rich domain (PRD) of maize γ-zein, and a bacteriophage T4 fibritin;
   wherein amino acid residues are added to the C-terminal end of the oligomerization domain such that the oligomerization domain from GCN4-pII or bacteriophage T4 fibritin does not terminate in an α-helix and the oligomerization domain from the PRD of maize γ-zein does not terminate in an amphipathic polyproline II helix;
   c) a nucleotide sequence encoding a signal peptide; and
   d) a nucleotide sequence encodinng an endoplasmic reticulum (ER) retention signal;
   wherein the nucleic acid encodes a soluble recombinant hemagglutinin (rHA) that forms a homotrimer.

4. A vector comprising the nucleotide sequence of claim 2.

5. A host cell expressing the rHA of claim 1.

6. A host cell transformed with the nucleotide sequence of claim 2.

7. A host cell transformed with the vector of claim 4.

8. A method of producing rHA, comprising providing a host cell comprising the nucleic acid of claim 3, and expressing the rHA in the host cell.

9. A method of expressing rHA within a plant comprising introducing a vector of claim 4 into a plant and expressing the rHA.

10. The method of claim 9, wherein the nucleic acid is introduced into the plant in a transient manner.

11. The method of claim 9, wherein the nucleic acid is introduced into the plant so that it is stably transformed.

12. A method of producing a recombinant hemagglutinin (rHA) in a plant comprising:

a) introducing a nucleic acid sequence into the plant, or portion thereof, the nucleic acid sequence comprising a regulatory region operatively linked to the nucleic acid of claim 3 and b) growing the transgenic plant, thereby producing the rHA.

13. The method of claim 12, wherein the nucleic acid is introduced into the plant in a transient manner.

14. The method of claim 12, wherein the nucleic acid is introduced into the plant so that it is stably transformed.

15. The rHA of claim 1, wherein the added amino acid residues are Ser-Ala-Ala.

16. The rHA of claim 1, wherein the ER retention signal is SEKDEL (SEQ ID NO:4) or HDEL (SEQ ID NO:5).

17. The nucleic acid of claim 3, wherein the added amino acid residues are Ser-Ala-Ala.

18. The nucleic acid of claim 3, wherein the ER retention signal is SEKDEL (SEQ ID NO:4) or HDEL (SEQ ID NO:5).

19. A vector comprising the nucleic acid of claim 3.

20. A host cell transformed with the nucleic acid of claim 3.

21. A host cell transformed with the vector of claim 19.

22. The rHA of claim 1, wherein the signal peptide is a protein disulfide isomerase (PDI) signal peptide.

23. The nucleic acid of claim 3, wherein the signal peptide is a protein disulfide isomerase (PDI) signal peptide.

* * * * *

SEQUENCE LISTING

<160> NUMBER OF SEQ ID NOS: 24

<210> SEQ ID NO 1
<211> LENGTH: 34
<212> TYPE: PRT
<213> ORGANISM: Artificial
<220> FEATURE:
<223> OTHER INFORMATION: Amino acid sequence of GCN4-pII peptide

<400> SEQUENCE: 1

Leu Lys Gln Ile Glu Asp Lys Ile Glu Glu Ile Leu Ser Lys Ile Tyr
1               5                   10                  15

His Ile Glu Asn Glu Ile Ala Arg Ile Lys Lys Leu Ile Gly Glu Ser
            20                  25                  30

Ala Ala

<210> SEQ ID NO 2
<211> LENGTH: 6
<212> TYPE: PRT
<213> ORGANISM: Artificial
<220> FEATURE:
<223> OTHER INFORMATION: Repeats of peptide PPPVHL

<400> SEQUENCE: 2

Pro Pro Pro Val His Leu
1               5

-continued

<210> SEQ ID NO 3
<211> LENGTH: 4
<212> TYPE: PRT
<213> ORGANISM: Artificial
<220> FEATURE:
<223> OTHER INFORMATION: Tetrapeptide linker

<400> SEQUENCE: 3

Gly Gly Ala Gly
1

<210> SEQ ID NO 4
<211> LENGTH: 6
<212> TYPE: PRT
<213> ORGANISM: Artificial
<220> FEATURE:
<223> OTHER INFORMATION: SEKDEL retention signal

<400> SEQUENCE: 4

Ser Glu Lys Asp Glu Leu
1               5

<210> SEQ ID NO 5
<211> LENGTH: 4
<212> TYPE: PRT
<213> ORGANISM: Artificial
<220> FEATURE:
<223> OTHER INFORMATION: HDEL retention signal

<400> SEQUENCE: 5

His Asp Glu Leu
1

<210> SEQ ID NO 6
<211> LENGTH: 24
<212> TYPE: PRT
<213> ORGANISM: Medicago sativa

<400> SEQUENCE: 6

Met Ala Lys Asn Val Ala Ile Phe Gly Leu Leu Phe Ser Leu Leu Val
1               5                   10                  15

Leu Val Pro Ser Gln Ile Phe Ala
            20

<210> SEQ ID NO 7
<211> LENGTH: 72
<212> TYPE: DNA
<213> ORGANISM: Medicago sativa

<400> SEQUENCE: 7
atggcgaaaa acgttgcgat tttcggttta ttgttttctc ttcttctgtt ggttccttct     60
cagatcttcg ct                                                         72

<210> SEQ ID NO 8
<211> LENGTH: 565
<212> TYPE: PRT
<213> ORGANISM: Influenza virus

<400> SEQUENCE: 8

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val His Ser Val Asn
    35                  40                  45

Leu Leu Glu Asp Ser His Asn Gly Lys Leu Cys Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
    195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
    275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
    355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
    435                 440                 445

-continued

```
Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 9
<211> LENGTH: 572
<212> TYPE: PRT
<213> ORGANISM: Artificial
<220> FEATURE:
<223> OTHER INFORMATION: Full length rHA with PDI signal peptide and
      transmembrane domain and cytoplasmic tail

<400> SEQUENCE: 9

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Ser His Asn Gly Lys
        50                  55                  60

Leu Cys Leu Leu Lys Gly Ile Ala Pro Leu Gln Leu Gly Asn Cys Ser
65                  70                  75                  80

Val Ala Gly Trp Ile Leu Gly Asn Pro Glu Cys Glu Leu Leu Ile Ser
                85                  90                  95

Lys Glu Ser Trp Ser Tyr Ile Val Glu Thr Pro Asn Pro Glu Asn Gly
                100                 105                 110

Thr Cys Tyr Pro Gly Tyr Phe Ala Asp Tyr Glu Glu Leu Arg Glu Gln
            115                 120                 125

Leu Ser Ser Val Ser Ser Phe Glu Arg Phe Glu Ile Phe Pro Lys Glu
        130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
                165                 170                 175

Lys Asn Gly Leu Tyr Pro Asn Leu Ser Lys Ser Tyr Val Asn Asn Lys
                180                 185                 190

Glu Lys Glu Val Leu Val Leu Trp Gly Val His His Pro Pro Asn Ile
            195                 200                 205

Gly Asn Gln Arg Ala Leu Tyr His Thr Glu Asn Ala Tyr Val Ser Val
        210                 215                 220

Val Ser Ser His Tyr Ser Arg Arg Phe Thr Pro Glu Ile Ala Lys Arg
225                 230                 235                 240
```

```
Pro Lys Val Arg Asp Gln Glu Gly Arg Ile Asn Tyr Tyr Trp Thr Leu
            245                 250                 255

Leu Glu Pro Gly Asp Thr Ile Ile Phe Glu Ala Asn Gly Asn Leu Ile
        260                 265                 270

Ala Pro Trp Tyr Ala Phe Ala Leu Ser Arg Gly Phe Gly Ser Gly Ile
    275                 280                 285

Ile Thr Ser Asn Ala Pro Met Asp Glu Cys Asp Ala Lys Cys Gln Thr
290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
        515                 520                 525

Glu Ser Met Gly Val Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
                565                 570

<210> SEQ ID NO 10
<211> LENGTH: 540
<212> TYPE: PRT
<213> ORGANISM: Artificial
<220> FEATURE:
<223> OTHER INFORMATION: ER-retained rHA using SEKDEL retention signal

<400> SEQUENCE: 10

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
            20                  25                  30
```

```
Ala Asn Asn Ser Thr Asp Thr Val Asp Thr Val Leu Glu Lys Asn Val
             35                  40                  45

Thr Val Thr His Ser Val Asn Leu Leu Glu Asp Ser His Asn Gly Lys
 50                  55                  60

Leu Cys Leu Leu Lys Gly Ile Ala Pro Leu Gln Leu Gly Asn Cys Ser
 65                  70                  75                  80

Val Ala Gly Trp Ile Leu Gly Asn Pro Glu Cys Glu Leu Leu Ile Ser
                 85                  90                  95

Lys Glu Ser Trp Ser Tyr Ile Val Glu Thr Pro Asn Pro Glu Asn Gly
            100                 105                 110

Thr Cys Tyr Pro Gly Tyr Phe Ala Asp Tyr Glu Glu Leu Arg Glu Gln
            115                 120                 125

Leu Ser Ser Val Ser Ser Phe Glu Arg Phe Glu Ile Phe Pro Lys Glu
130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
            165                 170                 175

Lys Asn Gly Leu Tyr Pro Asn Leu Ser Lys Ser Tyr Val Asn Asn Lys
            180                 185                 190

Glu Lys Glu Val Leu Val Leu Trp Gly Val His His Pro Pro Asn Ile
        195                 200                 205

Gly Asn Gln Arg Ala Leu Tyr His Thr Glu Asn Ala Tyr Val Ser Val
        210                 215                 220

Val Ser Ser His Tyr Ser Arg Arg Phe Thr Pro Glu Ile Ala Lys Arg
225                 230                 235                 240

Pro Lys Val Arg Asp Gln Glu Gly Arg Ile Asn Tyr Tyr Trp Thr Leu
                245                 250                 255

Leu Glu Pro Gly Asp Thr Ile Ile Phe Glu Ala Asn Gly Asn Leu Ile
            260                 265                 270

Ala Pro Trp Tyr Ala Phe Ala Leu Ser Arg Gly Phe Gly Ser Gly Ile
            275                 280                 285

Ile Thr Ser Asn Ala Pro Met Asp Glu Cys Asp Ala Lys Cys Gln Thr
290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
            355                 360                 365

Asp Gly Trp Tyr Gly Tyr His His Gln Asn Glu Gln Gly Ser Gly Tyr
            370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
            435                 440                 445
```

Leu Val Leu Glu Asn Glu Arg Thr Leu Asp Phe His Asp Ser Asn
450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
        515                 520                 525

Glu Ser Met Gly Val Tyr Ser Glu Lys Asp Glu Leu
530                 535                 540

<210> SEQ ID NO 11
<211> LENGTH: 538
<212> TYPE: PRT
<213> ORGANISM: Artificial
<220> FEATURE:
<223> OTHER INFORMATION: ER-retained rHA using HDEL retention signal

<400> SEQUENCE: 11

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Ser His Asn Gly Lys
50                  55                  60

Leu Cys Leu Leu Lys Gly Ile Ala Pro Leu Gln Leu Gly Asn Cys Ser
65                  70                  75                  80

Val Ala Gly Trp Ile Leu Gly Asn Pro Glu Cys Glu Leu Leu Ile Ser
                85                  90                  95

Lys Glu Ser Trp Ser Tyr Ile Val Glu Thr Pro Asn Pro Glu Asn Gly
            100                 105                 110

Thr Cys Tyr Pro Gly Tyr Phe Ala Asp Tyr Glu Glu Leu Arg Glu Gln
        115                 120                 125

Leu Ser Ser Val Ser Ser Phe Glu Arg Phe Glu Ile Phe Pro Lys Glu
130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
                165                 170                 175

Lys Asn Gly Leu Tyr Pro Asn Leu Ser Lys Ser Tyr Val Asn Asn Lys
            180                 185                 190

Glu Lys Glu Val Leu Val Leu Trp Gly Val His His Pro Pro Asn Ile
        195                 200                 205

Gly Asn Gln Arg Ala Leu Tyr His Thr Glu Asn Ala Tyr Val Ser Val
210                 215                 220

Val Ser Ser His Tyr Ser Arg Arg Phe Thr Pro Glu Ile Ala Lys Arg
225                 230                 235                 240

Pro Lys Val Arg Asp Gln Glu Gly Arg Ile Asn Tyr Tyr Trp Thr Leu
                245                 250                 255

Leu Glu Pro Gly Asp Thr Ile Ile Phe Glu Ala Asn Gly Asn Leu Ile
            260                 265                 270

```
Ala Pro Trp Tyr Ala Phe Ala Leu Ser Arg Gly Phe Ser Gly Ile
            275                 280                 285

Ile Thr Ser Asn Ala Pro Met Asp Glu Cys Asp Ala Lys Cys Gln Thr
    290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
        515                 520                 525

Glu Ser Met Gly Val Tyr His Asp Glu Leu
    530                 535

<210> SEQ ID NO 12
<211> LENGTH: 534
<212> TYPE: PRT
<213> ORGANISM: Artificial
<220> FEATURE:
<223> OTHER INFORMATION: Soluble rHA without transmembrane domain

<400> SEQUENCE: 12

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
            20                  25                  30

Ala Asn Asn Ser Thr Asp Thr Val Asp Thr Val Leu Glu Lys Asn

```
Lys Glu Ser Trp Ser Tyr Ile Val Glu Thr Pro Asn Pro Glu Asn Gly
            100                 105                 110

Thr Cys Tyr Pro Gly Tyr Phe Ala Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
                165                 170                 175

Lys Asn Gly Leu Tyr Pro Asn Leu Ser Lys Ser Tyr Val Asn Asn Lys
            180                 185                 190

Glu Lys Glu Val Leu Val Leu Trp Gly Val His His Pro Pro Asn Ile
        195                 200                 205

Gly Asn Gln Arg Ala Leu Tyr His Thr Glu Asn Ala Tyr Val Ser Val
    210                 215                 220

Val Ser Ser His Tyr Ser Arg Arg Phe Thr Pro Glu Ile Ala Lys Arg
225                 230                 235                 240

Pro Lys Val Arg Asp Gln Glu Gly Arg Ile Asn Tyr Tyr Trp Thr Leu
                245                 250                 255

Leu Glu Pro Gly Asp Thr Ile Ile Phe Glu Ala Asn Gly Asn Leu Ile
            260                 265                 270

Ala Pro Trp Tyr Ala Phe Ala Leu Ser Arg Gly Phe Gly Ser Gly Ile
        275                 280                 285

Ile Thr Ser Asn Ala Pro Met Asp Glu Cys Asp Ala Lys Cys Gln Thr
    290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510
```

```
Ser Glu Glu Ser Lys Leu Asn Arg Glu Lys Ile Asp Gly Val Lys Leu
        515                 520                 525

Glu Ser Met Gly Val Tyr
        530

<210> SEQ ID NO 13
<211> LENGTH: 568
<212> TYPE: PRT
<213> ORGANISM: Artificial
<220> FEATURE:
<223> OTHER INFORMATION: Soluble trimeric rHA using GCN4-pII trimeric
      peptide

<400> SEQUENCE: 13

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Ser His Asn Gly Lys
    50                  55                  60

Leu Cys Leu Leu Lys Gly Ile Ala Pro Leu Gln Leu Gly Asn Cys Ser
65                  70                  75                  80

Val Ala Gly Trp Ile Leu Gly Asn Pro Glu Cys Glu Leu Leu Ile Ser
                85                  90                  95

Lys Glu Ser Trp Ser Tyr Ile Val Glu Thr Pro Asn Pro Glu Asn Gly
            100                 105                 110

Thr Cys Tyr Pro Gly Tyr Phe Ala Asp Tyr Glu Glu Leu Arg Glu Gln
        115                 120                 125

Leu Ser Ser Val Ser Ser Phe Glu Arg Phe Glu Ile Phe Pro Lys Glu
    130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
                165                 170                 175

Lys Asn Gly Leu Tyr Pro Asn Leu Ser Lys Ser Tyr Val Asn Asn Lys
            180                 185                 190

Glu Lys Glu Val Leu Val Leu Trp Gly Val His His Pro Pro Asn Ile
        195                 200                 205

Gly Asn Gln Arg Ala Leu Tyr His Thr Glu Asn Ala Tyr Val Ser Val
    210                 215                 220

Val Ser Ser His Tyr Ser Arg Arg Phe Thr Pro Glu Ile Ala Lys Arg
225                 230                 235                 240

Pro Lys Val Arg Asp Gln Glu Gly Arg Ile Asn Tyr Tyr Trp Thr Leu
                245                 250                 255

Leu Glu Pro Gly Asp Thr Ile Ile Phe Glu Ala Asn Gly Asn Leu Ile
            260                 265                 270

Ala Pro Trp Tyr Ala Phe Ala Leu Ser Arg Gly Phe Gly Ser Gly Ile
        275                 280                 285

Ile Thr Ser Asn Ala Pro Met Asp Glu Cys Asp Ala Lys Cys Gln Thr
    290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335
```

```
Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
            355                 360                 365

Asp Gly Trp Tyr Gly Tyr His His Gln Asn Glu Gln Gly Ser Gly Tyr
            370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
            405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
            435                 440                 445

Leu Val Leu Leu Glu Asn Glu Arg Thr Leu Asp Phe His Asp Ser Asn
            450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
            485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
            515                 520                 525

Glu Ser Met Gly Val Tyr Leu Lys Gln Ile Glu Asp Lys Ile Glu Glu
            530                 535                 540

Ile Leu Ser Lys Ile Tyr His Ile Glu Asn Glu Ile Ala Arg Ile Lys
545                 550                 555                 560

Lys Leu Ile Gly Glu Ser Ala Ala
            565

<210> SEQ ID NO 14
<211> LENGTH: 574
<212> TYPE: PRT
<213> ORGANISM: Artificial
<220> FEATURE:
<223> OTHER INFORMATION: Soluble trimeric rHA using GCN4-pII trimeric
      peptide and retained in the ER

<400> SEQUENCE: 14

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
            20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Ser His Asn Gly Lys
            50                  55                  60

Leu Cys Leu Leu Lys Gly Ile Ala Pro Leu Gln Leu Gly Asn Cys Ser
65                  70                  75                  80

Val Ala Gly Trp Ile Leu Gly Asn Pro Glu Cys Glu Leu Leu Ile Ser
            85                  90                  95

Lys Glu Ser Trp Ser Tyr Ile Val Glu Thr Pro Asn Pro Glu Asn Gly
            100                 105                 110

Thr Cys Tyr Pro Gly Tyr Phe Ala Asp Tyr Glu Glu Leu Arg Glu Gln
            115                 120                 125
```

-continued

```
Leu Ser Ser Val Ser Ser Phe Glu Arg Phe Glu Ile Phe Pro Lys Glu
130                 135                 140
Ser Ser Trp Pro Asn His Thr Val Thr Gly Val Ser Ala Ser Cys Ser
145                 150                 155                 160
His Asn Gly Lys Ser Ser Phe Tyr Arg Asn Leu Leu Trp Leu Thr Gly
                165                 170                 175
Lys Asn Gly Leu Tyr Pro Asn Leu Ser Lys Ser Tyr Val Asn Asn Lys
            180                 185                 190
Glu Lys Glu Val Leu Val Leu Trp Gly Val His His Pro Pro Asn Ile
        195                 200                 205
Gly Asn Gln Arg Ala Leu Tyr His Thr Glu Asn Ala Tyr Val Ser Val
210                 215                 220
Val Ser Ser His Tyr Ser Arg Arg Phe Thr Pro Glu Ile Ala Lys Arg
225                 230                 235                 240
Pro Lys Val Arg Asp Gln Glu Gly Arg Ile Asn Tyr Tyr Trp Thr Leu
                245                 250                 255
Leu Glu Pro Gly Asp Thr Ile Ile Phe Glu Ala Asn Gly Asn Leu Ile
            260                 265                 270
Ala Pro Trp Tyr Ala Phe Ala Leu Ser Arg Gly Phe Gly Ser Gly Ile
        275                 280                 285
Ile Thr Ser Asn Ala Pro Met Asp Glu Cys Asp Ala Lys Cys Gln Thr
290                 295                 300
Pro Gln Gly Ala Ile Asn Ser Ser Leu Pro Phe Gln Asn Val His Pro
305                 310                 315                 320
Val Thr Ile Gly Glu Cys Pro Lys Tyr Val Arg Ser Ala Lys Leu Arg
                325                 330                 335
Met Val Thr Gly Leu Arg Asn Ile Pro Ser Ile Gln Ser Arg Gly Leu
            340                 345                 350
Phe Gly Ala Ile Ala Gly Phe Ile Glu Gly Gly Trp Thr Gly Met Val
        355                 360                 365
Asp Gly Trp Tyr Gly Tyr His His Gln Asn Glu Gln Gly Ser Gly Tyr
370                 375                 380
Ala Ala Asp Gln Lys Ser Thr Gln Asn Ala Ile Asn Gly Ile Thr Asn
385                 390                 395                 400
Lys Val Asn Ser Val Ile Glu Lys Met Asn Thr Gln Phe Thr Ala Val
                405                 410                 415
Gly Lys Glu Phe Asn Lys Leu Glu Arg Arg Met Glu Asn Leu Asn Lys
            420                 425                 430
Lys Val Asp Asp Gly Phe Leu Asp Ile Trp Thr Tyr Asn Ala Glu Leu
        435                 440                 445
Leu Val Leu Leu Glu Asn Glu Arg Thr Leu Asp Phe His Asp Ser Asn
450                 455                 460
Val Lys Asn Leu Tyr Glu Lys Val Lys Ser Gln Leu Lys Asn Asn Ala
465                 470                 475                 480
Lys Glu Ile Gly Asn Gly Cys Phe Glu Phe Tyr His Lys Cys Asn Asn
                485                 490                 495
Glu Cys Met Glu Ser Val Lys Asn Gly Thr Tyr Asp Tyr Pro Lys Tyr
            500                 505                 510
Ser Glu Glu Ser Lys Leu Asn Arg Glu Lys Ile Asp Gly Val Lys Leu
        515                 520                 525
Glu Ser Met Gly Val Tyr Leu Lys Gln Ile Glu Asp Lys Ile Glu Glu
530                 535                 540
```

```
Ile Leu Ser Lys Ile Tyr His Ile Glu Asn Glu Ile Ala Arg Ile Lys
545                 550                 555                 560

Lys Leu Ile Gly Glu Ser Ala Ala Ser Glu Asp Lys Glu Leu
                565                 570
```

<210> SEQ ID NO 15
<211> LENGTH: 593
<212> TYPE: PRT
<213> ORGANISM: Artificial
<220> FEATURE:
<223> OTHER INFORMATION: Soluble trimeric rHA using PRD trimeric peptide

<400> SEQUENCE: 15

```
Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
                20                  25                  30

Ala Asn Asn Ser Thr Asp Thr Val Asp Thr Val Leu Glu Lys Asn Val
            35                  40                  45

Thr Val Thr His Ser Val Asn Leu Leu Glu Asp Ser His Asn Gly Lys
        50                  55                  60

Leu Cys Leu Leu Lys Gly Ile Ala Pro Leu Gln Leu Gly Asn Cys Ser
65                  70                  75                  80

Val Ala Gly Trp Ile Leu Gly Asn Pro Glu Cys Glu Leu Leu Ile Ser
                85                  90                  95

Lys Glu Ser Trp Ser Tyr Ile Val Glu Thr Pro Asn Pro Glu Asn Gly
                100                 105                 110

Thr Cys Tyr Pro Gly Tyr Phe Ala Asp Tyr Glu Glu Leu Arg Glu Gln
            115                 120                 125

Leu Ser Ser Val Ser Ser Phe Glu Arg Phe Glu Ile Phe Pro Lys Glu
130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
                165                 170                 175

Lys Asn Gly Leu Tyr Pro Asn Leu Ser Lys Ser Tyr Val Asn Asn Lys
            180                 185                 190

Glu Lys Glu Val Leu Val Leu Trp Gly Val His His Pro Pro Asn Ile
        195                 200                 205

Gly Asn Gln Arg Ala Leu Tyr His Thr Glu Asn Ala Tyr Val Ser Val
    210                 215                 220

Val Ser Ser His Tyr Ser Arg Arg Phe Thr Pro Glu Ile Ala Lys Arg
225                 230                 235                 240

Pro Lys Val Arg Asp Gln Glu Gly Arg Ile Asn Tyr Tyr Trp Thr Leu
                245                 250                 255

Leu Glu Pro Gly Asp Thr Ile Ile Phe Glu Ala Asn Gly Asn Leu Ile
                260                 265                 270

Ala Pro Trp Tyr Ala Phe Ala Leu Ser Arg Gly Phe Gly Ser Gly Ile
            275                 280                 285

Ile Thr Ser Asn Ala Pro Met Asp Glu Cys Asp Ala Lys Cys Gln Thr
        290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335
```

```
Met Val Thr Gly Leu Arg Asn Ile Pro Ser Ile Gln Ser Arg Gly Leu
                340                 345                 350

Phe Gly Ala Ile Ala Gly Phe Ile Glu Gly Gly Trp Thr Gly Met Val
            355                 360                 365

Asp Gly Trp Tyr Gly Tyr His His Gln Asn Glu Gln Gly Ser Gly Tyr
        370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
            435                 440                 445

Leu Val Leu Leu Glu Asn Glu Arg Thr Leu Asp Phe His Asp Ser Asn
        450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
        515                 520                 525

Glu Ser Met Gly Val Tyr Gly Gly Ala Gly Pro Pro Pro Val His
530                 535                 540

Leu Pro Pro Val His Leu Pro Pro Val His Leu Pro Pro
545                 550                 555                 560

Val His Leu Pro Pro Val His Leu Pro Pro Val His Leu Pro
                565                 570                 575

Pro Pro Val His Leu Pro Pro Val His Leu Pro Pro Ser Ala
            580                 585                 590

Ala
```

<210> SEQ ID NO 16
<211> LENGTH: 599
<212> TYPE: PRT
<213> ORGANISM: Artificial
<220> FEATURE:
<223> OTHER INFORMATION: Soluble trimeric rHA using RDP trimeric peptide
      and retained in ER

<400> SEQUENCE: 16

```
Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
            20                  25                  30

Ala Asn Asn Ser Thr Asp Thr Val Asp Thr Val Leu Glu Lys Asn Val
        35                  40                  45

Thr Val Th

```
Lys Glu Ser Trp Ser Tyr Ile Val Glu Thr Pro Asn Pro Glu Asn Gly
                100                 105                 110

Thr Cys Tyr Pro Gly Tyr Phe Ala Asp Tyr Glu Glu Leu Arg Glu Gln
            115                 120                 125

Leu Ser Ser Val Ser Ser Phe Glu Arg Phe Glu Ile Phe Pro Lys Glu
        130                 135                 140

Ser Ser Trp Pro Asn His Thr Val Thr Gly Val Ser Ala Ser Cys Ser
145                 150                 155                 160

His Asn Gly Lys Ser Ser Phe Tyr Arg Asn Leu Leu Trp Leu Thr Gly
                165                 170                 175

Lys Asn Gly Leu Tyr Pro Asn Leu Ser Lys Ser Tyr Val Asn Asn Lys
            180                 185                 190

Glu Lys Glu Val Leu Val Leu Trp Gly Val His His Pro Pro Asn Ile
        195                 200                 205

Gly Asn Gln Arg Ala Leu Tyr His Thr Glu Asn Ala Tyr Val Ser Val
210                 215                 220

Val Ser Ser His Tyr Ser Arg Arg Phe Thr Pro Glu Ile Ala Lys Arg
225                 230                 235                 240

Pro Lys Val Arg Asp Gln Glu Gly Arg Ile Asn Tyr Tyr Trp Thr Leu
                245                 250                 255

Leu Glu Pro Gly Asp Thr Ile Ile Phe Glu Ala Asn Gly Asn Leu Ile
            260                 265                 270

Ala Pro Trp Tyr Ala Phe Ala Leu Ser Arg Gly Phe Gly Ser Gly Ile
        275                 280                 285

Ile Thr Ser Asn Ala Pro Met Asp Glu Cys Asp Ala Lys Cys Gln Thr
290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
        355                 360                 365

Asp Gly Trp Tyr Gly Tyr His His Gln Asn Glu Gln Gly Ser Gly Tyr
370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510
```

```
Ser Glu Glu Ser Lys Leu Asn Arg Glu Lys Ile Asp Gly Val Lys Leu
    515                 520                 525
Glu Ser Met Gly Val Tyr Gly Gly Ala Gly Pro Pro Pro Val His
530                 535                 540
Leu Pro Pro Pro Val His Leu Pro Pro Pro Val His Leu Pro Pro Pro
545                 550                 555                 560
Val His Leu Pro Pro Pro Val His Leu Pro Pro Pro Val His Leu Pro
                565                 570                 575
Pro Pro Val His Leu Pro Pro Pro Val His Leu Pro Pro Pro Ser Ala
            580                 585                 590
Ala Ser Glu Lys Asp Glu Leu
        595

<210> SEQ ID NO 17
<211> LENGTH: 1623
<212> TYPE: DNA
<213> ORGANISM: Influenza virus

<400> SEQUENCE: 17
```

| | | | | | |
|---|---|---|---|---|---|
| gggcccatgg | cgaaaaacgt | tgcgattttc | ggtttattgt | tttctcttct | tctgttggtt | 60 |
| ccttctcaga | tcttcgctga | cacaatatgt | ataggctacc | atgccaacaa | ctcaaccgac | 120 |
| actgttgaca | cagtacttga | aagaatgtg | acagtgacac | actctgtcaa | cctacttgag | 180 |
| gacagtcaca | atggaaaact | atgtctacta | aaaggaatag | ccccactaca | attgggtaat | 240 |
| tgcagcgttg | ccggatggat | cttaggaaac | ccagaatgcg | aattactgat | ttccaaggaa | 300 |
| tcatggtcct | acattgtaga | aacaccaaat | cctgagaatg | aacatgttca | cccagggtat | 360 |
| ttcgccgact | atgaggaact | gagggagcaa | ttgagttcag | tatcttcatt | tgagagattc | 420 |
| gaaatattcc | ccaaagaaag | ctcatggccc | aaccacaccg | taaccggagt | atcagcatca | 480 |
| tgctcccata | tgggaaaag | cagtttttac | agaaatttgc | tatggctgac | ggggaagaat | 540 |
| ggtttgtacc | caaacctgag | caagtcctat | gtaaacaaca | agagaaaga | agtccttgta | 600 |
| ctatggggtg | ttcatcaccc | gcctaacata | gggaaccaaa | gggcactcta | tcatacagaa | 660 |
| aatgcttatg | tctctgtagt | gtcttcacat | tatagcagaa | gattcacccc | agaaatagcc | 720 |
| aaaagaccca | agtaagaga | tcaggaagga | agaatcaact | actactggac | tctgctggaa | 780 |
| cctggggata | caataatatt | tgaggcaaat | ggaaatctaa | tagcgccatg | gtatgctttt | 840 |
| gcactgagta | gaggctttgg | atcaggaatc | atcacctcaa | atgcaccaat | ggatgaatgt | 900 |
| gatgcgaagt | gtcaaacacc | tcagggagct | ataaacagca | gtcttccttt | ccagaatgta | 960 |
| cacccagtca | aataggaga | gtgtccaaag | tatgtcagga | gtgcaaaatt | aaggatggtt | 1020 |
| acaggactaa | ggaacatccc | atccattcaa | tccagaggtt | tgtttggagc | cattgccggt | 1080 |
| ttcattgaag | ggggtggac | tggaatggta | gatgggtggt | atggttatca | tcatcagaat | 1140 |
| gagcaaggat | ctggctatgc | tgcagatcaa | aaaagtacac | aaaatgccat | taacgggatt | 1200 |
| acaaacaagg | tcaattctgt | aattgagaaa | atgaacactc | aattcacagc | tgtgggcaaa | 1260 |
| gagttcaaca | aattggaaag | aaggatggaa | aacttaaata | aaaagttga | tgatgggttt | 1320 |
| ctagacattt | ggacatataa | tgcagaattg | ttggttctac | tggaaaatga | aaggactttg | 1380 |
| gatttccatg | actccaatgt | gaagaatctg | tatgagaaag | taaaaagcca | attaaagaat | 1440 |
| aatgccaaag | aaataggaaa | cgggtgtttt | gagttctatc | acaagtgtaa | caatgaatgc | 1500 |
| atggagagtg | tgaaaaatgg | tacctatgac | tatccaaaat | attccgaaga | atcaaagtta | 1560 |

```
aacagggaga aaattgatgg agtgaaattg gaatcaatgg gagtatacta agagctcagg    1620
cct                                                                 1623

<210> SEQ ID NO 18
<211> LENGTH: 219
<212> TYPE: DNA
<213> ORGANISM: Influenza virus

<400> SEQUENCE: 18
ggtacctatg actatccaaa atattccgaa gaatcaaagt taaacaggga gaaaattgat    60
ggagtgaaat tggaatcaat gggagtatac cagattctgg cgatctactc aactgtcgcc   120
agttccctgg ttcttttggt ctccctgggg gcaatcagct tctggatgtg ttccaatggg   180
tctttgcagt gtagaatatg catctaagag ctcaggcct                           219

<210> SEQ ID NO 19
<211> LENGTH: 123
<212> TYPE: DNA
<213> ORGANISM: Artificial
<220> FEATURE:
<223> OTHER INFORMATION: ER-retained SEKDEL gene fragment

<400> SEQUENCE: 19
ggtacctatg actatccaaa atattccgaa gaatcaaagt taaacaggga gaaaattgat    60
ggagtgaaat tggaatcaat gggagtatac tctgagaagg atgaacttta agagctcagg   120
cct                                                                 123

<210> SEQ ID NO 20
<211> LENGTH: 117
<212> TYPE: DNA
<213> ORGANISM: Artificial
<220> FEATURE:
<223> OTHER INFORMATION: ER-retained HDEL gene fragment

<400> SEQUENCE: 20
ggtacctatg actatccaaa atattccgaa gaatcaaagt taaacaggga gaaaattgat    60
ggagtgaaat tggaatcaat gggagtatac cacgatgaac tttaagagct caggcct      117

<210> SEQ ID NO 21
<211> LENGTH: 207
<212> TYPE: DNA
<213> ORGANISM: Artificial
<220> FEATURE:
<223> OTHER INFORMATION: GCN4-pII gene fragment

<400> SEQUENCE: 21
ggtacctatg actatccaaa atattccgaa gaatcaaagt taaacaggga gaaaattgat    60
ggagtgaaat tggaatcaat gggagtatac ctcaaacaaa tcgaagacaa gatcgaagag   120
atcctctcga aaatctacca catcgaaaac gagattgcca ggatcaagaa gctcataggc   180
gagtcagcag cctaagagct caggcct                                       207

<210> SEQ ID NO 22
<211> LENGTH: 225
<212> TYPE: DNA
<213> ORGANISM: Artificial
<220> FEATURE:
<223> OTHER INFORMATION: ER-retained GCN4-pII gene fragment
```

```
<400> SEQUENCE: 22
ggtacctatg actatccaaa atattccgaa gaatcaaagt taaacaggga gaaaattgat    60
ggagtgaaat tggaatcaat gggagtatac ctcaaacaaa tcgaagacaa gatcgaagag   120
atcctctcga aaatctacca catcgaaaac gagattgcca ggatcaagaa gctcataggc   180
gagtcagcag cctctgagaa ggatgaactt taagagctca ggcct                   225

<210> SEQ ID NO 23
<211> LENGTH: 279
<212> TYPE: DNA
<213> ORGANISM: Zea maize

<400> SEQUENCE: 23
ggtacctatg actatccaaa atattccgaa gaatcaaagt taaacaggga gaaaattgat    60
ggagtgaaat tggaatcaat gggagtatac ggaggcgctg gcccaccgcc agttcatcta   120
ccgcctccgg tgcatctgcc acctccggtt cacctgccac ctccggtgca tctcccaccg   180
ccagtccacc tgccgcctcc ggtccacctg ccaccgcctg tccatgtgcc gccaccggtt   240
catctgccgc ctccatcagc agcctaagag ctcaggcct                          279

<210> SEQ ID NO 24
<211> LENGTH: 297
<212> TYPE: DNA
<213> ORGANISM: Artificial
<220> FEATURE:
<223> OTHER INFORMATION: ER-retained gene fragment

<400> SEQUENCE: 24
ggtacctatg actatccaaa atattccgaa gaatcaaagt taaacaggga gaaaattgat    60
ggagtgaaat tggaatcaat gggagtatac ggaggcgctg gcccaccgcc agttcatcta   120
ccgcctccgg tgcatctgcc acctccggtt cacctgccac ctccggtgca tctcccaccg   180
ccagtccacc tgccgcctcc ggtccacctg ccaccgcctg tccatgtgcc gccaccggtt   240
catctgccgc ctccatcagc agcctctgag aaggatgaac tttaagagct caggcct      297
```